United States Patent
Tanabe et al.

(10) Patent No.: US 11,898,130 B2
(45) Date of Patent: Feb. 13, 2024

(54) CELL CULTURE EQUIPMENT

(71) Applicants: I Peace, Inc., Palo Alto, CA (US);
FANUC CORPORATION, Yamanashi (JP)

(72) Inventors: Koji Tanabe, Palo Alto, CA (US);
Ryoji Hiraide, Kyoto (JP); Kenta Suto, Palo Alto, CA (US); Kazunori Ban, Yamanashi (JP); Satoshi Kinoshita, Yamanashi (JP)

(73) Assignees: Peace, Inc., Palo Alto, CA (US);
FANUC CORPORATION, Yamanashi (JP)

( * ) Notice: Subject to any disclaimer, the term of this patent is extended or adjusted under 35 U.S.C. 154(b) by 374 days.

(21) Appl. No.: 17/269,944

(22) PCT Filed: Aug. 20, 2019

(86) PCT No.: PCT/JP2019/032384
§ 371 (c)(1),
(2) Date: Feb. 19, 2021

(87) PCT Pub. No.: WO2020/040118
PCT Pub. Date: Feb. 27, 2020

(65) Prior Publication Data
US 2021/0222107 A1    Jul. 22, 2021

Related U.S. Application Data

(60) Provisional application No. 62/766,597, filed on Aug. 20, 2018.

(51) Int. Cl.
C12M 1/12    (2006.01)
C12M 1/32    (2006.01)
C12M 1/00    (2006.01)

(52) U.S. Cl.
CPC ............ C12M 25/02 (2013.01); C12M 23/12 (2013.01); C12M 23/34 (2013.01); C12M 41/14 (2013.01)

(58) Field of Classification Search
CPC ...... C12M 25/00; C12M 23/12; C12M 23/34; C12M 41/14; C12M 25/02
(Continued)

(56) References Cited

U.S. PATENT DOCUMENTS

| | | | |
|---|---|---|---|
| 4,748,124 A | 5/1988 | Vogler | |
| 5,449,617 A | 9/1995 | Falkenberg et al. | |
| 5,510,262 A * | 4/1996 | Stephanopoulos | C12M 25/18 435/297.2 |

(Continued)

FOREIGN PATENT DOCUMENTS

| | | |
|---|---|---|
| EP | 3 480 290 A1 | 5/2019 |
| JP | S61-108373 A | 5/1986 |

(Continued)

OTHER PUBLICATIONS

WO-2016093321-A1 Machine English translation (Year: 2016).*
(Continued)

*Primary Examiner* — Michael L Hobbs
*Assistant Examiner* — Lenora A Abel
(74) *Attorney, Agent, or Firm* — Studebaker & Brackett PC

(57) ABSTRACT

A cell culture equipment comprising a culture component permeable member 10 that is permeable to culture components, a culture vessel 30 that covers one side of the culture component permeable member 10 and holds a cell-containing medium, and a medium holding vessel 40 that covers the other side of the culture component permeable member 10 and holds a medium.

20 Claims, 27 Drawing Sheets

(58) Field of Classification Search
USPC .................................................... 435/297.1
See application file for complete search history.

(56) References Cited

U.S. PATENT DOCUMENTS

| | | | |
|---|---|---|---|
| 5,593,580 A | 1/1997 | Kopf | |
| 8,507,266 B2* | 8/2013 | Welter | ................... C12M 21/08 |
| | | | 435/303.1 |
| 2009/0068742 A1 | 3/2009 | Yamanaka | |
| 2009/0298181 A1 | 12/2009 | Watanabe et al. | |
| 2012/0077220 A1 | 3/2012 | Mizutani et al. | |
| 2013/0157353 A1 | 6/2013 | Dijkhuizen Borgart et al. | |
| 2014/0335608 A1* | 11/2014 | Tanaka | ................... C12M 23/14 |
| | | | 435/303.1 |
| 2015/0306641 A1 | 10/2015 | Suzuki et al. | |
| 2016/0355774 A1 | 12/2016 | Konishi et al. | |
| 2018/0245041 A1 | 8/2018 | Tanabe et al. | |

FOREIGN PATENT DOCUMENTS

| | | |
|---|---|---|
| JP | H06-181749 A | 7/1994 |
| JP | H11-501866 A | 2/1999 |
| JP | 2006-030465 A | 2/2006 |
| JP | 2006-304733 A | 11/2006 |
| JP | 2008-017716 A | 1/2008 |
| JP | 4183742 B1 | 11/2008 |
| JP | 2011-004613 A | 1/2011 |
| JP | 2012-147678 A | 8/2012 |
| JP | 2014-064475 A | 4/2014 |
| JP | 2014-114997 A | 6/2014 |
| WO | 2010/131715 A1 | 11/2010 |
| WO | 2013/114845 A1 | 8/2013 |
| WO | 2015/122528 A1 | 8/2015 |
| WO | WO-2016093321 A1 * | 6/2016 ............. C12M 1/00 |
| WO | 2017/038887 A1 | 3/2017 |
| WO | 2017/056695 A1 | 4/2017 |
| WO | 2018/003073 A1 | 1/2018 |

OTHER PUBLICATIONS

International Preliminary Report on Patentability (Chapter II) issued in PCT/JP2019/032384; completed Dec. 21, 2020. lo X.

International Search Report issued in PCT/JP2019/032384; dated Nov. 26, 2019.

* cited by examiner

TRA-1-60

CELL CULTURE EQUIPMENT

TECHNICAL FIELD

The present invention relates to cell technology, and to a cell culture equipment.

BACKGROUND ART

Embryonic stem cells (ES cells) are stem cells that have been established from human and mouse early embryos. ES cells exhibit pluripotency, allowing them to differentiate into all types of cells present in the living body. At present, human ES cells can be used in cell transplant therapy for treating many diseases including Parkinson's disease, juvenile onset diabetes and leukemia. However, there are drawbacks associated with transplantation of ES cells. Notably, ES cell transplantation can trigger immune rejection reactions similar to the rejection reactions that occur after unsuccessful organ transplantation. Moreover, there are many ethical criticisms and objections to the use of ES cells that have been established by destroying human embryos.

Under these circumstances, Shinya Yamanaka, a professor at Kyoto University succeeded in establishing induced pluripotent stem cells (iPS cells) by introducing four genes, namely the OCT3/4, KLF4, c-MYC and SOX2 genes, into somatic cells. For this, Professor Yamanaka received the Nobel Prize in Physiology or Medicine in 2012 (see for example Patent Documents 1 and 2). iPS cells are ideal pluripotent stem cells because they are free from rejection reactions and ethical concerns. Consequently, iPS are expected to be used for cell transplantation therapy.

CITATION LIST

Patent Documents

Patent Document 1: Japanese Patent No. 4183742
Patent Document 2: Japanese Patent Application Publication No. 2014-114997

SUMMARY

Technical Problem

There is demand for devices capable of efficiently culturing a variety of cells in addition to iPS cells. An object of the present invention is to provide a cell culture equipment capable of efficiently culturing cells.

Solution to Problem

Embodiments of the present invention provide a cell culture equipment including a culture component permeable member that is permeable to culture components, a culture vessel for holding a cell-containing medium and culturing cells that covers one side of the culture component permeable member, and a medium holding vessel for holding a medium that covers the other side of the culture component permeable member.

In the cell culture equipment, the culture component permeable member may be a semipermeable membrane.

The cell culture equipment may include a culture-side plate and a medium-side plate provided with respective openings, the culture-side plate and the medium-side plate interposing the culture component permeable member, wherein the cell-containing medium in the culture vessel is capable of being brought into contact with the culture component permeable member through the openings in the culture-side plate, and the medium in the medium holding vessel is capable of being brought into contact with the culture component permeable member through the openings in the medium-side plate.

In the cell culture equipment, the culture-side plate may be dark colored.

In the cell culture equipment, the culture vessel and medium holding vessel may be detachable.

In the cell culture equipment, the surface of the culture-side plate may be cell non-adhesive.

In the cell culture equipment, the surface of the culture-side plate may be protein non-adhesive.

In the cell culture equipment, the surface of the culture-side plate may be cell adhesive.

In the cell culture equipment, the surface of the culture component permeable member may be cell non-adhesive.

In the cell culture equipment, the surface of the culture component permeable member may be protein non-adhesive.

In the cell culture equipment, the surface of the culture component permeable member may be cell adhesive.

In the cell culture equipment, the culture component permeable member may be cell adhesive.

In the cell culture equipment, the culture component permeable member may be cell non-adhesive.

In the cell culture equipment, it may be that outside air does not enter the culture vessel and the medium holding vessel in the case where the culture vessel and the medium holding vessel are in a sealed state.

In the cell culture equipment, it may be that cells, microorganisms, viruses and dust from outside the culture vessel and the medium holding vessel do not enter the culture vessel and the medium holding vessel in the case where the culture vessel and the medium holding vessel are in a sealed state.

In the cell culture equipment, it may be that substances within the culture vessel and the medium holding vessel do not leak out of the culture vessel and the medium holding vessel in the case where the culture vessel and the medium holding vessel are in a sealed state.

In the cell culture equipment, there may be no exchange of gasses between the inside and outside of the culture vessel and the medium holding vessel in the case where the culture vessel and the medium holding vessel are in a sealed state.

In the cell culture equipment, it may be that at least one of carbon dioxide gas, nitrogen gas and oxygen gas is not supplied to the inside of the culture vessel and the medium holding vessel in the case where the culture vessel and the medium holding vessel are in a sealed state.

In the cell culture equipment, the medium inside the culture vessel and the medium holding vessel may be maintained within a predetermined pH range.

In the cell culture equipment, the culture vessel may be embedded in a gas impermeable material.

In the cell culture equipment, the medium holding vessel may be embedded in a gas impermeable material.

The cell culture equipment may further comprise a packing disposed between the culture component permeable member and the culture vessel.

In the cell culture equipment, the packing may be disposed between the culture vessel and the outer circumference of the culture component permeable member.

In the cell culture equipment, the outer diameter of the packing may be greater than the outer diameter of the culture component permeable member.

The cell culture equipment may further include a packing disposed between the culture component permeable member and the medium holding vessel.

In the cell culture equipment, the packing may be disposed between the medium holding vessel and the outer circumference of the culture component permeable member.

In the cell culture equipment, the outer diameter of the packing may be greater than the outer diameter of the culture component permeable member.

In the cell culture equipment, the inside of the culture vessel may be cell non-adhesive.

In the cell culture equipment, the inside of the culture vessel may be protein non-adhesive.

In the cell culture equipment, the inside of the culture vessel may be cell adhesive.

Embodiments of the present invention also provide a sealable culture vessel for culturing cells, wherein the culture vessel includes a supply inlet for supplying fluid to the inside of the culture vessel and an outlet for discharging fluid from the inside of the culture vessel, and the supply inlet and outlet are sealable.

In the culture vessel, the supply equipment for supplying the fluid to the supply inlet may be detachable.

In the culture vessel, the supply equipment may be connected to the supply inlet through a needleless supply connector.

In the culture vessel, the discharge equipment for discharging the fluid to the outlet may be detachable.

In the culture vessel, the discharge equipment may be connected to the outlet through a needleless discharge connector.

In the culture vessel, in the case where the supply equipment for supplying the fluid to the supply inlet and the discharge equipment for discharging the fluid to the outlet are detachable, the fluid inside the culture vessel may move to the inside of the discharge equipment in the case where fluid is supplied from the supply equipment to the inside of the culture vessel.

In the culture vessel, the air inside the culture vessel may move to the inside of the discharge equipment in the case where medium is supplied to the inside of the culture vessel from the supply equipment.

In the culture vessel, the medium inside the culture vessel may move to the inside of the discharge equipment in the case where medium is supplied to the inside of the culture vessel from the supply equipment.

In the culture vessel, the medium may contain cells.

In the culture vessel, outside air may not enter the culture vessel in the case where fluid is supplied to the inside of the culture vessel from the supply equipment.

The culture vessel may comprise a window.

In the culture vessel, the window may be provided with a transparent heater.

The culture vessel may comprise a temperature regulator for regulating the temperature inside the culture vessel.

The culture vessel may comprise a thermometer for measuring the temperature inside the culture vessel.

In the culture vessel, outside air may not enter the culture vessel in the case where the culture vessel is in a sealed state.

In the culture vessel, it may be that cells, microorganisms, viruses and dust from outside the culture vessel do not enter the culture vessel in the case where the culture vessel is in a sealed state.

In the culture vessel, it may be that substances within the culture vessel do not leak out of the culture vessel in the case where the culture vessel is in a sealed state.

In the culture vessel, there may be no exchange of gasses between the inside and outside the culture vessel in the case where the culture vessel is in a sealed state.

In the culture vessel, it may be that at least any one of carbon dioxide gas, nitrogen gas and oxygen gas is not supplied to the inside of the culture vessel in the case where the culture vessel is in a sealed state.

In the culture vessel, the medium inside the culture vessel may be maintained within a predetermined pH range.

In the culture vessel, the culture vessel may be embedded in a gas impermeable material.

In the culture vessel, the tilt of the culture vessel may be adjustable.

Stem cells may be expansion cultured in the culture vessel.

In the culture vessel, the stem cells may be iPS cells, ES cells or somatic stem cells.

In the culture vessel, stem cells may be induced by culturing cells introduced with an induction factor.

In the culture vessel, an induction factor may be added to medium in the culture vessel to introduce the induction factor into cells being cultured in the culture vessel.

In the culture vessel, stem cells may be induced from cells introduced with the induction factor.

In the culture vessel, the stem cells may be iPS cells.

In the culture vessel, the cells may be blood cells.

In the culture vessel, cells introduced with the induction factor may be cultured in the culture vessel and induced to generate cells of a different type.

In the culture vessel, an induction factor may be added to medium in the culture vessel to introduce the induction factor into cells being cultured in the culture vessel, and the cells are then induced to generate cells of a different type.

In the culture vessel, the induction factor may be RNA.

In the culture vessel, the induction factor may be contained in a Sendai virus.

In the culture vessel, the induction factor may be contained in a plasmid.

Cells may be cultured in the culture vessel.

In the culture vessel, the cells may be one or more selected from the blood cells, neural cells, myocardial cells, epithelial cells, mesenchymal cells and liver cells.

In the culture vessel, cells may be suspension cultured in the culture vessel.

In the culture vessel, cells may be adhesion cultured in the culture vessel.

In the culture vessel, cells may be cultured in gel medium in the culture vessel.

The interior of the culture vessel may be cell non-adhesive.

The interior of the culture vessel may be protein non-adhesive.

The interior of the culture vessel may be cell adhesive.

Other embodiments of the invention provide a culture apparatus comprising the above culture vessel and an imaging apparatus for imaging at least either one of the medium and the cells in the culture vessel.

In the culture apparatus, the imaging apparatus may image the cells through a telecentric lens.

The culture apparatus may further include an image processor that applies a high-pass filter to the images obtained by the imaging apparatus.

In the culture apparatus, the image processor may extract cells or cell colonies in the images by applying a watershed algorithm to the images to which the high-pass filter has been applied.

In the culture apparatus, the image processor may apply the distance transform method to the images before applying the watershed algorithm to the images.

In the culture apparatus, the image processor may calculate the size of the extracted cells or cell colonies.

In the culture apparatus, the image processor may calculate the number of extracted cells or cell colonies.

The culture apparatus may further comprise a relationship storage for storing the relationship between the turbidity of the medium and the density of the cells or cell colonies in the medium, and may further comprise an image processor that calculates the value of the turbidity of the medium in the culture vessel based on images obtained by the imaging apparatus and then calculates the value of the density of the imaged cells or cell colonies based on the calculated turbidity value and the stored relationship.

The culture apparatus may further comprise an image processor that calculates the value of the density of the cells or cell colonies in the medium from the number of extracted cells or cell colonies and the ratio of the volume of the region imaged by the imaging apparatus relative to the volume of the culture vessel.

The culture apparatus may further comprise a relationship storage that stores a relationship between the color of the medium and the pH of the medium, and may further comprise an image processor that calculates the value of the color of the medium in the culture vessel in an image obtained by the imaging apparatus, and then calculates the value of the pH of the imaged medium based on the calculated color value and the stored relationship.

Other embodiments of the invention provide a sealable medium holding vessel for holding a medium, comprising an inlet for supplying fluid to the inside of the medium holding vessel and an outlet for discharging fluid from the inside of the medium holding vessel, wherein the inlet and outlet are sealable.

In the medium holding vessel, the supply equipment for supplying the fluid to the inlet may be detachable.

In the medium holding vessel, the supply equipment may be connected to the inlet through a needleless supply connector.

In the medium holding vessel, the discharge equipment for discharging the fluid to the outlet is detachable.

In the medium holding vessel, the discharge equipment may be connected to the outlet through a needleless discharge connector.

In the medium holding vessel, in the case where the supply equipment for supplying the fluid to the inlet and the discharge equipment for discharging the fluid to the outlet are detachable, the fluid inside the medium holding vessel may move to the inside of the discharge equipment in the case where fluid is supplied from the supply equipment to the inside of the medium holding vessel.

In the medium holding vessel, the air inside the medium holding vessel may move to the inside of the discharge equipment in the case where medium is supplied to the inside of the medium holding vessel from the supply equipment.

In the medium holding vessel, the medium inside the medium holding vessel may move to the inside of the discharge equipment in the case where medium is supplied to the inside of the medium holding vessel from the supply equipment.

In the medium holding vessel, outside air may not enter the medium holding vessel in the case where fluid is supplied to the inside of the medium holding vessel from the supply equipment.

The medium holding vessel may further comprise a temperature regulator for regulating the temperature within the medium holding vessel.

The medium holding vessel may further comprise a thermometer for measuring the temperature within the medium holding vessel.

In the medium holding vessel, outside air may not enter the medium holding vessel in the case where the medium holding vessel is in a sealed state.

In the medium holding vessel, it may be that cells, microorganisms, viruses and dust from outside the medium holding vessel do not enter the medium holding vessel in the case where the medium holding vessel is in a sealed state.

In the medium holding vessel, it may be that substances within the medium holding vessel do not leak out of the medium holding vessel in the case where the medium holding vessel is in a sealed state.

In the medium holding vessel, there may be no exchange of gasses between the inside and outside of the medium holding vessel in the case where the medium holding vessel is in a sealed state.

In the medium holding vessel, it may be that at least one of carbon dioxide gas, nitrogen gas and oxygen gas is not supplied to the inside of the medium holding vessel in the case where the medium holding vessel is in a sealed state.

In the medium holding vessel, the medium inside the medium holding vessel may be maintained within a predetermined pH range.

In the medium holding vessel, the medium holding vessel may be embedded in a gas impermeable material.

The medium holding vessel may be equipped with a rectifying plate disposed within the medium holding vessel.

In the medium holding vessel, one or a plurality of discharge ports for supplying medium to the inside of the medium holding vessel is provided, wherein the one or a plurality of discharge ports communicates with the inlet.

In the medium holding vessel, a discharge block having one or a plurality of discharge ports is capable of being inserted into the inside of the medium holding vessel, wherein the one or a plurality of discharge ports is for supplying medium to the inside of the medium holding vessel, and wherein the one or a plurality of discharge ports is capable of communicating with the inlet.

The medium holding vessel may be provided with an opening for venting air from inside the medium holding vessel to the outside in the case where medium is introduced into the medium holding vessel.

In the medium holding vessel, a medium conduit may be connected to the inlet and outlet of the medium holding vessel.

In the medium holding vessel, medium may be allowed to circulate inside the medium holding vessel and the medium conduit.

In the medium holding vessel, the inside of the medium holding vessel may be sealed by connecting the medium conduit with the medium holding vessel.

The medium holding vessel may be connected to a culture vessel for culturing cells.

In the medium holding vessel, the inside of the medium holding vessel may be sealed by connecting the medium holding vessel to the culture vessel.

Embodiments of the invention provide a sealable medium conduit comprising a supply inlet for supplying fluid to the inside of the medium conduit and an outlet for discharging the fluid inside the medium conduit, wherein the supply inlet and outlet are sealable.

In the medium conduit, the supply equipment for supplying the fluid to the supply inlet may be detachable.

In the medium conduit, the supply equipment may be connected to the supply inlet through a needleless supply connector.

In the medium conduit, the discharge equipment for discharging the fluid from the outlet may be detachable.

In the medium conduit, the discharge equipment may be connected to the outlet through a needleless discharge connector.

In the medium conduit, in the case where the supply equipment for supplying the fluid to the supply inlet and the discharge equipment for discharging the fluid to the outlet are detachable, the fluid inside the medium conduit may move to the inside of the discharge equipment in the case where fluid is supplied to the inside of the medium conduit from the supply equipment.

The medium conduit may further comprise a fluid machine for moving fluid.

In the medium conduit, in the case where the supply equipment for supplying the fluid to the supply inlet and the discharge equipment for discharging the fluid to the outlet are detachable, fluid may be supplied from the supply equipment to the medium conduit and the fluid inside the medium conduit may move to the inside of the discharge equipment in the case where the fluid machine is operated.

In the medium conduit, the air inside the medium conduit may move to the inside of the discharge equipment in the case where medium is supplied to the inside of the medium conduit from the supply equipment.

In the medium conduit, the medium inside the medium conduit may move to the inside of the discharge equipment in the case where medium is supplied to the inside of the medium conduit from the supply equipment.

In the medium conduit, outside air may not enter the inside of the medium conduit in the case where fluid is supplied to the inside of the medium conduit from the supply equipment.

The medium conduit may comprise a temperature regulator for regulating the temperature inside the medium conduit.

The medium conduit may be provided with a thermometer for measuring the temperature inside the medium conduit.

In the medium conduit, outside air may not enter the medium conduit in the case where the medium conduit is in a sealed state.

In the medium conduit, it may be that microorganisms, viruses and dust from outside the culture vessel do not enter the medium conduit in the case where the medium conduit is in a sealed state.

In the medium conduit, it may be that substances inside the medium conduit do not leak out of the medium conduit in the case where the medium conduit is in a sealed state.

In the medium conduit, it may be that there is no exchange of gasses between the inside and outside the medium conduit in the case where the medium conduit is in a sealed state.

In the medium conduit, it may be that at least one of carbon dioxide gas, nitrogen gas and oxygen gas is not supplied to the inside of the medium conduit in the case where the medium conduit is in a sealed state.

In the medium conduit, the medium inside the medium conduit may be maintained within a predetermined pH range.

The medium conduit may be shielded from outside air by an outside air shielding member for the medium conduit.

The medium conduit may be embedded in a gas impermeable material.

At least part of the medium conduit may be a hole provided in the member.

In the medium conduit, the fluid machine may be shielded from outside air by an outside air shielding member for the fluid machine.

In the medium conduit, the medium conduit may be shielded from outside air by an outside air shielding member for the medium conduit, the medium conduit and the pump head of the fluid machine may be disposed within the outside air shielding member for the medium conduit, and a driver connected to the pump head of the fluid machine may be disposed outside the outside air shielding member for the medium conduit.

In the medium conduit, the pump head and the driver may be detachable.

In the medium conduit, the outside air shielding member for the medium conduit containing the medium conduit and the pump head may be disposable.

In the medium conduit, the driver may be supported on a driver holding member, and the outside air shielding member for the medium conduit and the driver holding member may be detachable.

In the medium conduit, it may be that there is no exchange of gasses between the inside and outside of the outside air shielding member for the medium conduit in the case where the driver holding member is detached from the outside air shielding member for the medium conduit.

The medium conduit may be connected to a culture vessel for culturing cells.

In the medium conduit, the medium may circulate within the medium conduit and the culture vessel.

In the medium conduit, the inside of the medium conduit may be sealed by connecting the medium conduit to the culture vessel.

The medium conduit may be connected to a medium holding vessel for holding medium.

In the medium conduit, the medium may circulate within the medium conduit and the medium holding vessel.

In the medium conduit, the inside of the medium conduit may be sealed by connecting the medium conduit to the medium holding vessel.

Cells may be cultured inside the medium conduit.

The inside of the medium conduit may be cell nonadhesive.

The inside of the medium conduit may be protein nonadhesive.

The inside of the medium conduit may be cell adhesive.

Embodiments of the invention also provide a culture apparatus comprising the above medium conduit and an imaging apparatus for imaging at least either one of the medium and the cells inside the medium conduit.

In the culture apparatus, the imaging apparatus may image the cells through a telecentric lens.

The culture apparatus may further comprise an image processer that applies a high-pass filter to the images obtained by the imaging apparatus.

In the culture apparatus, the image processer may extract cells or cell colonies in the images by applying a watershed algorithm to the images to which the high-pass filter has been applied.

In the culture apparatus, the image processer may apply the distance transform method to the images before applying the watershed algorithm to the images.

In the culture apparatus, the image processer may calculate the size of the extracted cells or cell colonies.

In the culture apparatus, the image processer may calculate the number of extracted cells or cell colonies.

The culture apparatus may comprise a relationship storage for storing the relationship between the turbidity of the medium and the density of the cells or cell colonies in the medium, and may further comprise an image processor that calculates the value of the turbidity of the medium in the medium conduit based on images obtained by the imaging apparatus and then calculates the value of the density of the imaged cells or cell colonies based on the calculated turbidity value and the stored relationship.

The culture apparatus may further comprise an image processor that calculates the value of the density of the cells or cell colonies in the medium conduit from the number of extracted cells or cell colonies and the ratio of the volume of the region imaged by the imaging apparatus relative to the volume of the medium conduit as a whole.

The culture apparatus may further comprise a relationship storage that stores the relationship between the color of the medium and the pH of the medium, and may further comprise an image processor that calculates the value of the color of the medium in the medium conduit in an image obtained by the imaging apparatus, and then calculates the value of the pH of the imaged medium based on the calculated color value and the stored relationship.

Other embodiments of the invention provide a plate for use in the case where cells are cultured, wherein the plate has openings and is used overlaid with a culture component permeable member, which is a membrane that allows permeation of culture components.

This plate may be dark colored.

The size of the part without openings in the plate may be larger than the size of a cell or a cell colony made up of cells.

The surface of the plate may be cell adhesive.

Advantageous Effects of Invention

A cell culture equipment capable of efficiently culturing cells can be provided by the present invention.

DESCRIPTION OF EMBODIMENTS

Embodiments of the invention are explained below. In the descriptions of the following drawings, identical or similar parts are indicated by identical or similar symbols. However, the drawings are schematic. Thus, specific dimensions and the like should be determined with reference to the explanations below. Of course, in some parts the dimensional relationships and ratios also differ between drawings.

Figure 1:
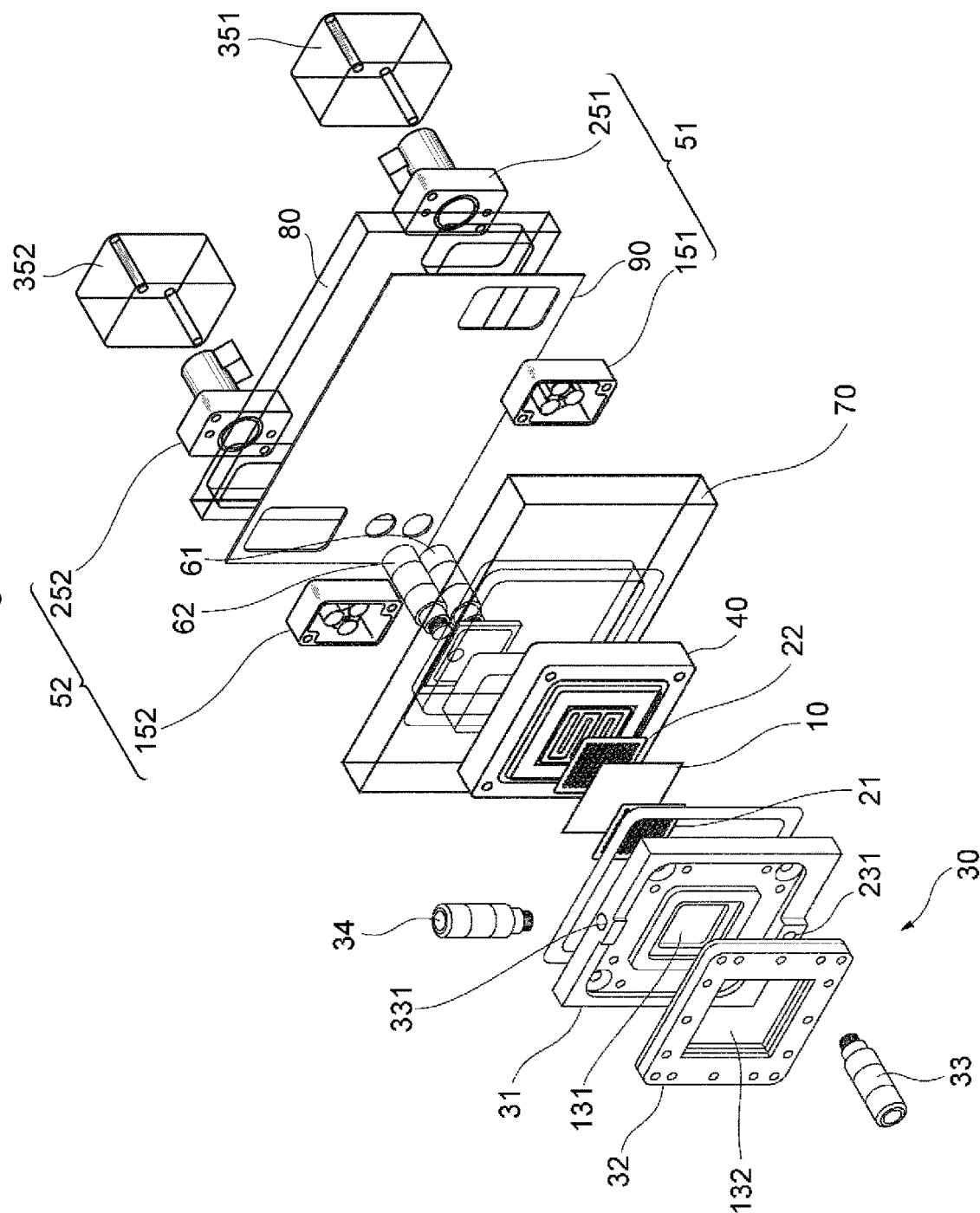
FIG. 1 is an exploded perspective view of a cell culture equipment according to an embodiment.

As shown in FIG. 1, the cell culture equipment according to the embodiment includes a culture component permeable member 10, a culture vessel 30 for culturing cells that covers one side of the culture component permeable member 10 and holds cell-containing medium, and a medium holding vessel 40 that covers the other side of the culture component permeable member 10 and holds medium. The cell-containing medium in the culture vessel 30 is able to contact the culture component permeable member 10. The medium in the medium holding vessel 40 is also able to contact the culture component permeable member 10. The medium in the medium holding vessel 40 does not contain cells.

The culture component permeable member 10 allows active components of the medium in the medium holding vessel 40 to pass into the cell-containing medium in the culture vessel 30. The culture component permeable member 10 may allow waste in the cell-containing medium in the culture vessel 30 to pass into the medium in the medium holding vessel 40. A semipermeable membrane or mesh for example may be used as the culture component permeable member 10. The semipermeable membrane may be a dialysis membrane.

When the culture component permeable member 10 is a semipermeable membrane, the molecular weight fraction of the semipermeable membrane is at least 0.1 KDa, or at least 10 KDa, or at least 50 KDa for example. The semipermeable membrane consists for example of a cellulose ester, ethyl cellulose, cellulose ester, regenerated cellulose, polysulfone, polyacrylonitrile, polymethyl methacrylate, ethylene vinyl alcohol copolymer, polyester polymer alloy, polycarbonate, polyamide, cellulose acetate, cellulose diacetate, cellulose triacetate, copper ammonium rayon, saponified cellulose or a hemophan membrane, phosphatidyl choline membrane, vitamin E coated membrane or the like.

When the culture component permeable member 10 is a mesh, the mesh has holes that are smaller than the cells or cell colonies being cultured in the culture vessel 30. This prevents the cells or cell colonies inside the culture vessel 30 from moving into the medium holding vessel 40. The material of the mesh is not particularly limited but may be a resin or metal for example. The surface of the culture component permeable member 10 may be cell non-adhesive.

The cell culture equipment according to the embodiment may include a culture-side plate 21 and a medium-side plate 22 each provided with openings on either side of the culture component permeable member 10. The culture component permeable member 10 is sandwiched between the culture-side plate 21 and medium-side plate 22, which thus support the culture component permeable member 10 in such a way that deflection of the culture component permeable member 10 due to the pressure of the cell-containing medium in the culture vessel 30 and the medium in the medium holding vessel 40 is suppressed. The culture component permeable member 10 is thus prevented from contacting the inner walls of the culture vessel 30 and medium holding vessel 40 due to pressure fluctuations. The culture-side plate 21 and medium-side plate 22 have a hardness that does not fluctuate under pressure from the cell-containing medium inside the culture vessel 30 and the medium inside the medium holding vessel 40. The materials of the culture-side plate 21 and the medium-side plate 22 are not particularly limited and may be resin or metal for example. The surface of the culture-side plate 21 may be cell non-adhesive. It should be noted that, if the culture component permeable member 10 is not deflected by pressure from the cell-containing medium inside the culture vessel 30 and the medium inside the medium holding vessel 40, the culture-side plate 21 and medium-side plate 22 may be omitted.

The culture-side plate 21 has openings through which the cell-containing culture in the culture vessel 30 can contact the culture component permeable member 10. The medium-side plate 22 also has openings through which the medium inside the medium holding vessel 40 can contact the culture component permeable member 10. The components of the cell-containing medium inside the culture vessel 30 and the components of the medium inside the medium holding vessel 40 can pass through the culture component permeable member 10 through the openings in the culture-side plate 21. The shapes of the openings in the culture-side plate 21 and the medium-side plate 22 are not particularly limited but may be circular for example. The size of the openings in the culture-side plate 21 and the medium-side plate 22 is within a range at which deflection of the culture component permeable member 10 can be prevented. The openings are provided in the culture-side plate 21 and the medium-side plate 22 either randomly or in a lattice.

The culture-side plate 21 may have a dark color such as black for example. If the culture-side plate 21 has a dark color, the cells in the cell-containing medium can be confirmed visually or imaged with high contrast against the dark background of the culture-side plate 21. If the size of the area of the part without openings in the culture-side plate 21 is greater than the size of a cell or cell colony, the cells or cell colonies can be easily confirmed visually or imaged with high contrast against the dark background of the part without openings in the culture-side plate 21. It should be noted that the light irradiating the cells or cell colonies can also be adjusted so that the cells or cell colonies can be confirmed visually or imaged even if the culture component permeable member 10 or culture-side plate 21 is transparent.

The culture vessel 30 and medium holding vessel 40 may be fixed with a screw, pin, electromagnet or the like. The contact area of the culture vessel 30 is in close contact with at least part of one surface of the culture-side plate 21. At least part of the other surface of the culture-side plate 21 is also in close contact with at least part of one surface of the culture component permeable member 10. At least part of the other surface of the culture component permeable member 10 is also in close contact with at least part of one surface of the medium-side plate 22. At least part of the other surface of the medium-side plate 22 is also in close contact with the contact part of the medium holding vessel 40. A packing or the like may be used appropriately when bringing these parts into contact. A packing may be disposed for example between the culture component permeable member 10 and the culture vessel 30. A packing may be disposed between the outer circumference of the culture component permeable member 10 and the culture vessel 30. The outer diameter of the packing disposed between the culture component permeable member 10 and the culture vessel 30 may be greater than the outer diameter of the culture component permeable member 10. A packing may be disposed for example between the culture component permeable member 10 and the medium holding vessel 40. A packing may be disposed between the outer circumference of the culture component permeable member 10 and the medium holding vessel 40. The outer diameter of the packing disposed between the culture component permeable member 10 and the medium holding vessel 40 may be greater than the outer diameter of the culture component permeable member 10.

Figure 2:
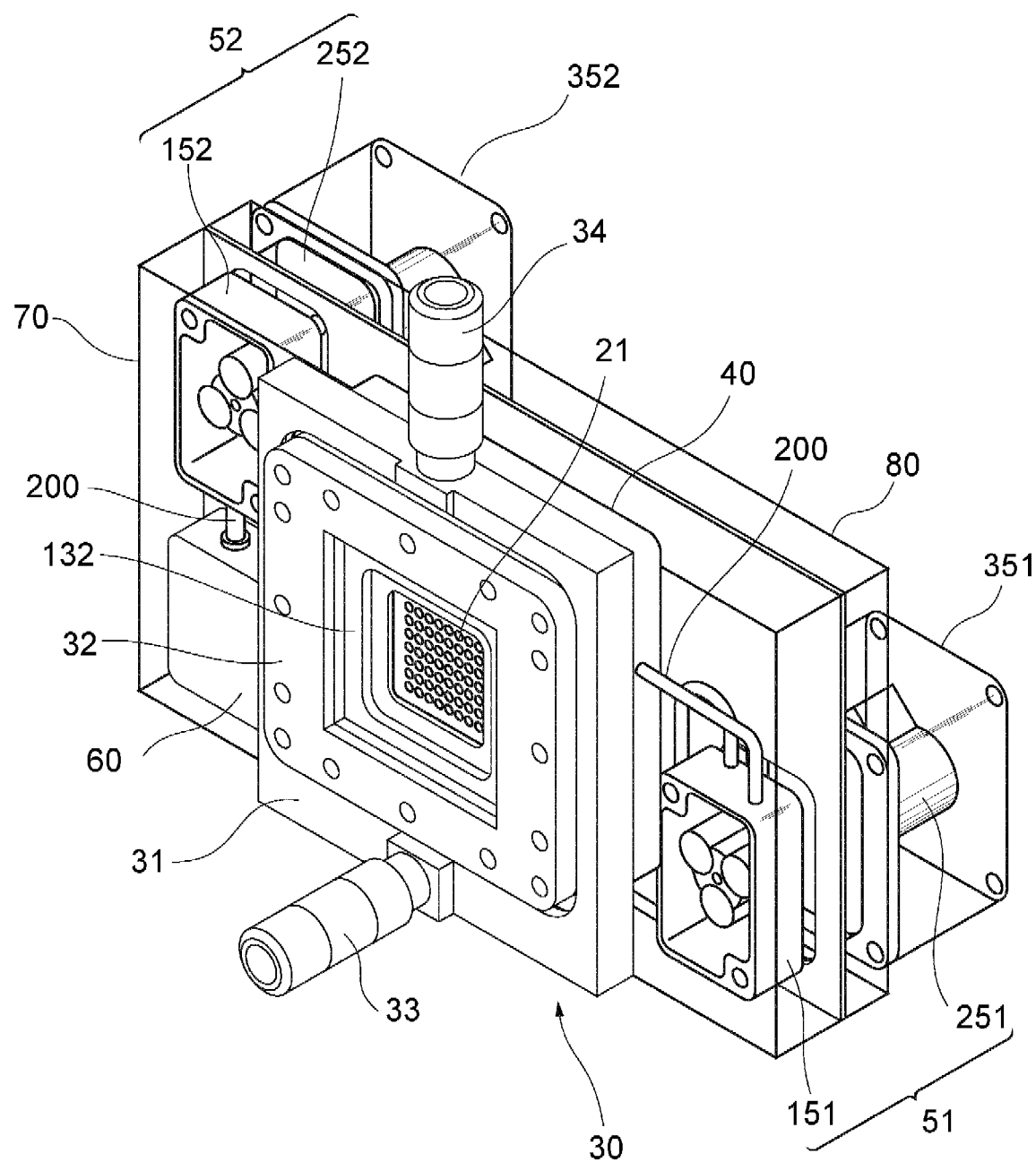
FIG. 2 is a perspective view of a cell culture equipment according to an embodiment.

The culture vessel 30 includes a housing 31 and a cover 32 covering the housing 31. The housing 31 and cover 32 may be integrated. The inner wall of the culture vessel 30 may be coated with a cell non-adhesive substance such as poly 2-hydroxyethyl methacrylate (poly-HEMA), or else the inner wall of the culture vessel 30 may itself be cell non-adhesive so that cells do not adhere to the inner wall of the culture vessel 30. The housing 31 is provided with an opening 131 through which the culture component permeable member 10 is exposed through the openings in the culture-side plate 21. As shown in FIG. 2, the cover 32 of the culture vessel 30 is provided with a window 132 through which the cell-containing medium in the culture vessel 30 can be observed. Glass or resin for example may be used as the material of the window 132.

The cell culture equipment according to the embodiment may include a temperature regulator for heating or cooling the window 132. The temperature regulator may be a transparent heater such as a transparent conductive film that is disposed on the window 132 and heats the window. Alternatively, the cell culture equipment according to the embodiment may include a temperature regulator that heats and cools the housing 31 or cover 32 of the culture vessel 30. The temperature of the cell-containing medium inside the culture vessel 30 can be regulated by using the temperature regulator to adjust the temperature of any one of the housing 31, the cover 32 and the window 132. The cell culture equipment according to the embodiment may include a thermometer for measuring the temperature of the cell-containing medium inside the culture vessel 30. The thermometer may measure the temperature of the cell-containing medium based on the temperature of the culture vessel 30 without contacting the cell-containing medium itself, or it may measure the temperature of the cell-containing medium directly through contact with the cell-containing medium. In the latter case, the temperature regulator may be subjected to feedback control so that the cell-containing medium is maintained at a predetermined temperature. The temperature of the cell-containing medium is adjusted to from 20° C. to 45° C. for example.

As shown in FIG. 1, the culture vessel 30 is provided with a supply inlet 231 for supplying fluid to the inside of the culture vessel 30 and an outlet 331 for discharging the fluid inside the culture vessel 30. For example, the plug 33 shown in FIG. 2, which can be connected to a supply equipment such as a bag, bellows or syringe for supplying the fluid, is inserted into the supply inlet 231. The supply equipment may be a fluid machine such as a pump. It should be noted that an injection device can be connected directly to the supply inlet 231 shown in FIG. 1. When the supply equipment is detachable from the supply inlet 231 and the supply equipment is not connected to the supply inlet 231, the supply inlet 231 can be sealed so that there is no exchange of fluid between the inside and outside of the culture vessel 30 through the supply inlet 231.

The plug 33 may be a needleless connector. The needleless connector may be a split septum type or mechanical bulb type connector. When the plug 33 is a split septum type needleless connector, the plug 33 includes a disc valve with a slit. When fluid is supplied to the inside of the culture vessel 30, the supply equipment or a conduit connected to the supply equipment is inserted into the slit in the disc valve. When a supply equipment or a conduit connected to a supply equipment is not inserted into the slit, the slit is sealed. When a supply equipment or a conduit connected to a supply equipment is inserted into the slit, the disc valve is in close contact with the outer circumference of the supply equipment or the conduit connected to the supply equipment. Consequently, even when a supply equipment or a conduit connected to a supply equipment is inserted into the plug 33, outside air does not penetrate the inside of the culture vessel 30 through the plug 33. It should be noted that the plug 33 can be a connector into which a needle is inserted.

Also, for example the plug 34 shown in FIG. 2, which can be connected to a discharge equipment such as a bag, bellows or syringe for discharging the fluid inside the culture vessel 30, is inserted into the outlet 331. The discharge equipment may be a fluid machine such as a pump. It should be noted that the discharge equipment can be connected directly to the outlet 331 shown in FIG. 1. The discharge equipment may actively aspirate the fluid in the culture vessel 30. Alternatively, the internal capacity of the discharge equipment may increase passively according to the pressure inside the culture vessel 30, causing the discharge equipment to receive fluid expelled from the culture vessel 30. When the discharge equipment is detachable from the outlet 331 and the discharge equipment is not connected to the outlet 331, the outlet 331 can be sealed so that there is no exchange of fluid between the inside and outside of the culture vessel 30 through the outlet 331. The plug 34 may be a needleless connector. The needleless connector may be a split septum type or mechanical bulb type connector. When the discharge equipment or a conduit connected to the discharge equipment is inserted into the plug 34, outside air does not penetrate the inside of the culture vessel 30 through the plug 34. It should be noted that the plug 34 can be connector into which a needle is inserted.

For example, when the culture vessel 30 is in close contact with the medium holding vessel 40 through the inserted culture-side plate 21, the inserted culture component permeable member 10 and the inserted medium-side plate 22 and the culture vessel 30 contains air, cell-containing medium can be made to enter the culture vessel 30 shown in FIG. 2 by injecting the cell-containing medium into the culture vessel 30 through the supply inlet 231 as air inside the culture vessel 30 is discharged through the outlet 331. The air layer inside the culture vessel 30 can also be completely eliminated. However, an air layer may remain inside the culture vessel 30. When the culture vessel 30 already contains cell-containing medium, the cell-containing medium already inside the culture vessel 30 can be discharged through the outlet 331 shown in FIG. 1 as new cell-containing medium is injected into the culture vessel 30 through the supply inlet 231, thereby replacing at least part of the cell-containing medium inside the culture vessel 30 shown in FIG. 2.

The cell culture equipment according to the embodiment may include a culture vessel supporting member that can support the culture vessel 30 and also be capable of adjusting the tilt of the culture vessel 30. Gas such as air inside the culture vessel 30 can be easily discharged by adjusting the tilt of the culture vessel 30.

The supply inlet 231 and outlet 331 of the culture vessel 30 can be blocked by plugs or the like. It is also possible to block the plug 33 and plug 34 attached to the supply inlet 231 and outlet 331, respectively, of the culture vessel 30. Alternatively, the supply inlet 231 of the culture vessel 30 can be shielded from the outside by connecting it to a supply equipment, while the outlet 331 of the culture vessel 30 can be shielded from the outside by connecting it to a discharge equipment. When the supply inlet 231 and outlet 331 are blocked and the culture vessel 30 is in close contact with the medium holding vessel 40 as shown in FIG. 2, the inside of the culture vessel 30 is shielded from the air outside the culture vessel 30. This prevents outside air from penetrating the inside of the culture vessel 30, suppressing changes in the pH of the cell-containing medium inside the culture vessel 30 so that the pH is maintained within a predetermined range. The predetermined range of the pH of the cell-containing medium is from 6.0 to 9.0 for example. Based on the inventors' findings, as the cells can be cultured in a completely shielded enclosed space, it is not necessary to actively supply carbon dioxide gas, nitrogen gas, oxygen gas or the like to the inside of the culture vessel 30. Thus, it is not necessary to dispose the culture vessel 30 inside a $CO_2$ incubator. Furthermore, the cleanliness inside the culture vessel 30 is maintained as no cells, microorganisms, viruses or dust from outside the culture vessel 30 can penetrate the inside of the sealed culture vessel 30. Therefore, it is not necessary to dispose the culture vessel 30 in a clean room. The culture vessel 30 may be enveloped in a gas impermeable substance. In other words, the culture vessel 30 may be embedded in a gas impermeable substance.

The cells cultured inside the culture vessel 30 may be stem cells such as artificial pluripotent stem cells (iPS cells), embryonic stem cells (ES cells) or somatic stem cells, or they may be cells other than stem cells. The somatic stem cells may be mesenchymal stem cells. The stem cells may be expansion cultured inside the culture vessel 30. The cells cultured inside the culture vessel 30 may be cells introduced with an induction factor that are then induced to generate stem cells. Alternatively, the cells being cultured inside the culture vessel 30 may be cells not introduced with an induction factor, and an induction factor may be added to the cell-containing medium inside the culture vessel 30 to introduce the induction factor into the cells and induce them to generate stem cells. Induction of cells into stem cells may be referred to initialization. The cells that are induced to generate stem cells may be blood cells. The cells cultured inside the culture vessel 30 may be cells introduced with an induction factor that are then induced to generate cells of a different type. The cells cultured inside the culture vessel 30 may be cells not introduced with an induction factor, and an induction factor may be added the cell-containing medium inside the culture vessel 30 to introduce the induction factor into the cells and induce them to generate cells of a different type. Induction of a different type of differentiated cells from differentiated cells may be referred to transdifferentiation, lineage reprogramming, or cell fate reprogramming. Stem cells may be induced into cells inside the culture vessel 30. The induction factor may be RNA or a protein. The induction factor may be contained in plasmids, Sendai viruses, adenoviruses, lentiviruses or retroviruses for example. The cells cultured inside the culture vessel 30 may be uninduced cells. Examples of cells that can be cultured inside the culture vessel 30 include blood cells, nerve cells, myocardial cells, epithelial cells, vascular endothelial cells, mesenchymal cells, fibroblasts, hepatocytes, insulin producing cells, retinal pigment epithelial cells and corneal cells. Examples of blood cells include T cells, B cells, NK cells, NKT cells, megakaryocytes, macrophages, granulocytes, neutrophils, eosinophils, hematopoietic stem cells, blood stem/progenitor cells, red blood cells, white blood cells and platelets. Examples of nerve cells include neural cells, glial cells, oligodendrocytes and neural stem cells. Examples of myocardial cells include myocardial stem cells, cardiomyocytes and pacemaker cells. Examples of epithelial cells include keratinocytes, intestinal epithelial cells, oral epithelial cells and corneal epithelial cells. Examples of mesenchymal cells include dermal cells, osteoblasts, fat cells, muscle cells and cartilage cells. The cells may form cell clumps (colonies) in cell-containing medium. The cells may be animal cells such as human cells, or insect cells, or plant cells.

The cell-containing medium may be gelatinous. In this case, the cell-containing medium may contain at least one type of polymeric compound selected from the group consisting of gellan gum, deacylated gellan gum, hyaluronic acid, rhamsan gum, diutan gum, xanthan gum, carrageenan, fucoidan, pectin, pectic acid, pectinic acid, heparan sulfate, heparin, heparitin sulfate, keratosulfate, chondroitin sulfate, dermatan sulfate, rhamnan sulfate and salts of these. The cell-containing medium may contain methyl cellulose. Aggregation of cells can be further suppressed by including methyl cellulose.

Alternatively, the cell-containing medium may contain at least one temperature-sensitive gel selected from poly(glycerol monomethacrylate) (PGMA), poly(2-hydroxypropyl methacrylate) (PHPMA), poly(N-isopropylacrylamide) (PNIPAM), and amine terminated, carboxylic acid terminated, maleimide terminated, N-hydroxysuccinimide (NHS) ester terminated and triethoxysilane terminated poly (N-isopropylacrylamide-co-acrylamide), poly(N-isopropylacrylamide-co-acrylic acid), poly(N-isopropylacrylamide-co-butylacrylate), poly(N-isopropylacrylamide-co-methacrylic acid), poly(N-isopropylacrylamide-co-methacrylic acid-co-octadecyl acrylate) and N-isopropylacrylamide.

In these disclosures, gelatinous media or gel media include polymer media.

Figure 3:
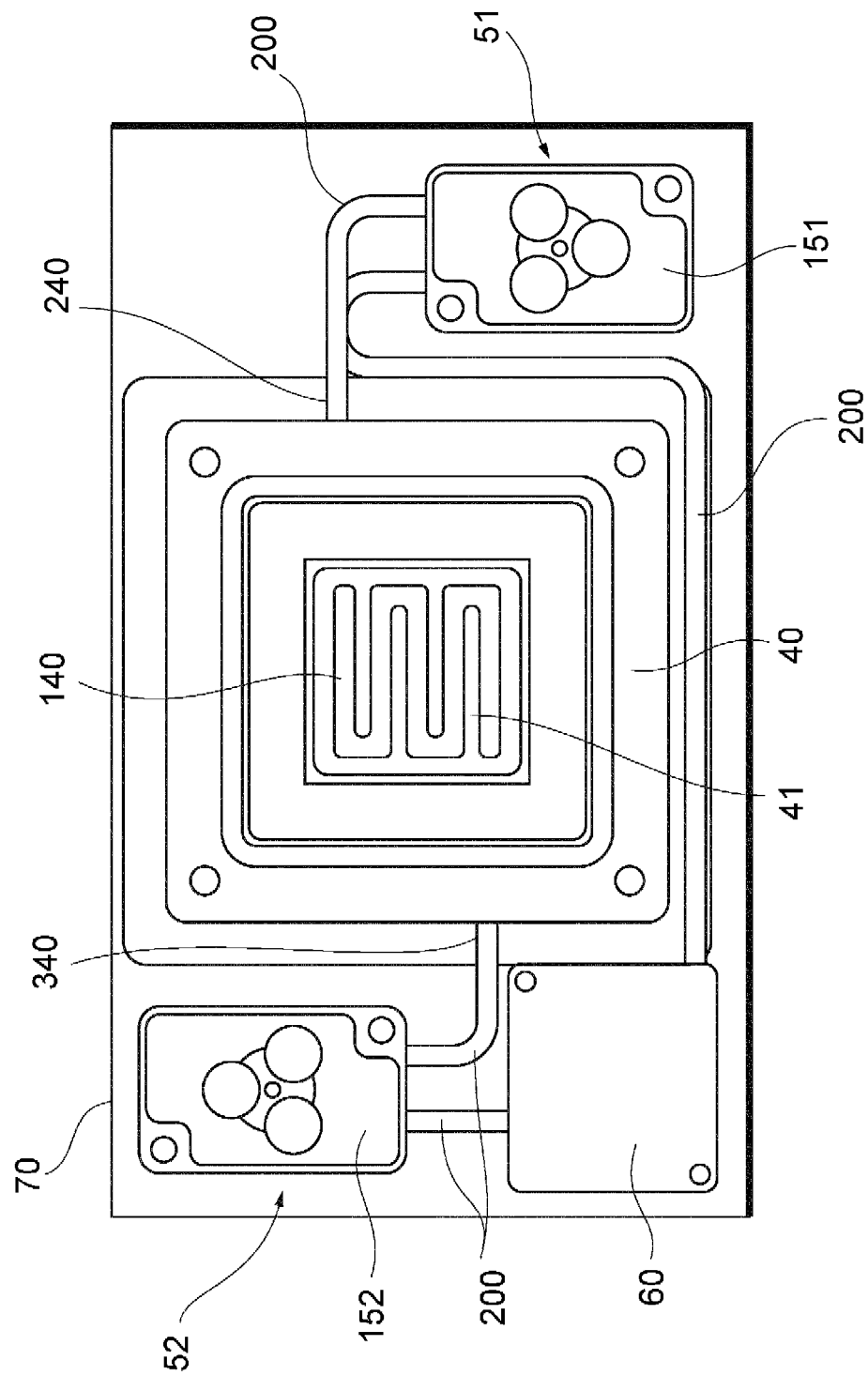
FIG. 3 is a front view of a part of a cell culture equipment according to an embodiment.

The medium holding vessel 40 shown in FIG. 1 includes an opening 140 shown in FIG. 3 for exposing the culture component permeable member 10 through the openings in the medium-side plate 22. The opening 140 is covered by the culture component permeable member 10 shown in FIG. 1. The medium holding vessel 40 shown in FIG. 3 also includes an inlet 240 for introducing fluid into the medium holding vessel 40 and an outlet 340 for discharging the fluid inside the medium holding vessel 40. Multiple rectifying plates 41 may be disposed within the medium holding vessel 40. A plurality of the rectifying plates 41 are disposed so as to project alternately from the facing inner walls of the medium holding vessel 40 for example.

For example, when the medium holding vessel 40 is in close contact with the culture vessel 30 through the inserted medium-side plate 22, the inserted culture component permeable member 10 and the inserted culture-side plate 21 shown in FIG. 1 and the medium holding vessel 40 contains air, cell medium can be made to enter the medium holding vessel 40 by injecting cell medium into the medium holding vessel 40 from the inlet 240 while discharging the air inside the medium holding vessel 40 through the outlet 340 shown in FIG. 3. When the medium holding vessel 40 already contains medium, cell medium can be injected into the medium holding vessel 40 through the inlet 240 as the cell medium in the medium holding vessel 40 is discharged through the outlet 340, causing cell medium to flow into the medium holding vessel 40.

When the plurality of the rectifying plates 41 are disposed within the medium holding vessel 40, the medium flows along the plurality of the rectifying plates 41 from the inlet 240 towards the outlet 340 in the medium holding vessel 40. This secures opportunities for components of the medium to contact the culture component permeable member 10.

Figure 4:
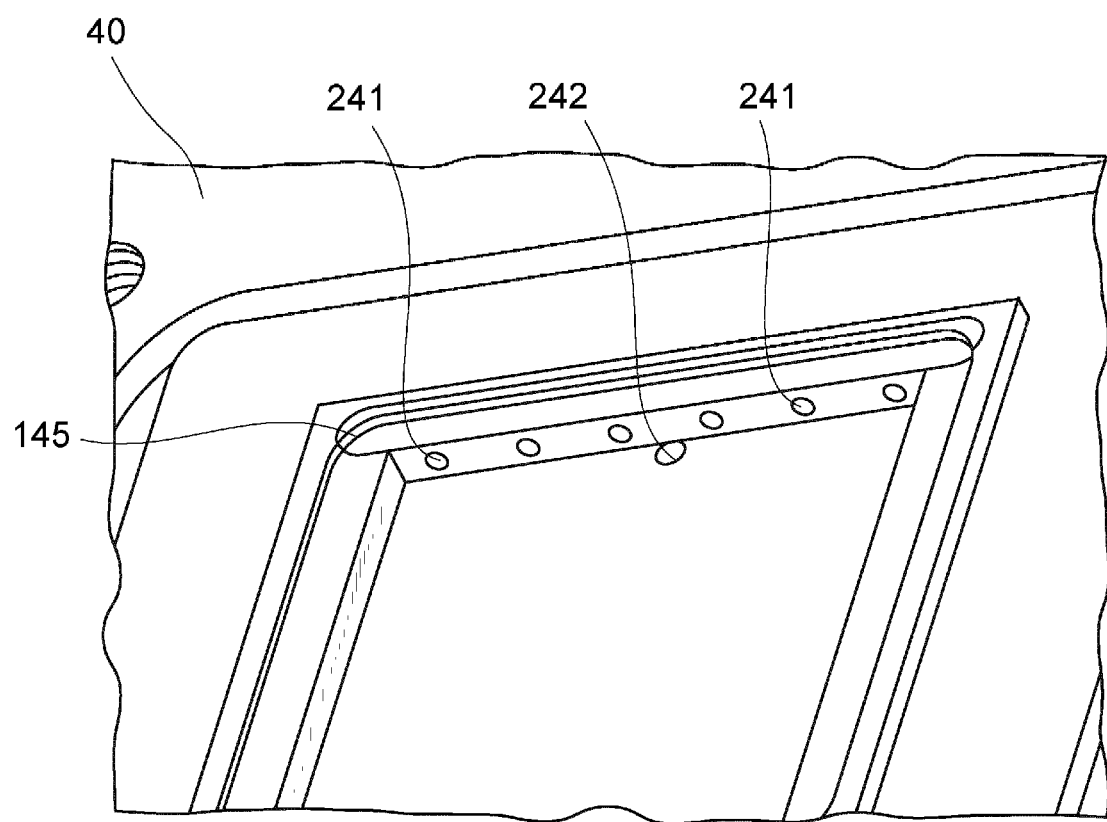
FIG. 4 is a perspective view of a part of a cell culture equipment according to an embodiment.
Figure 5:
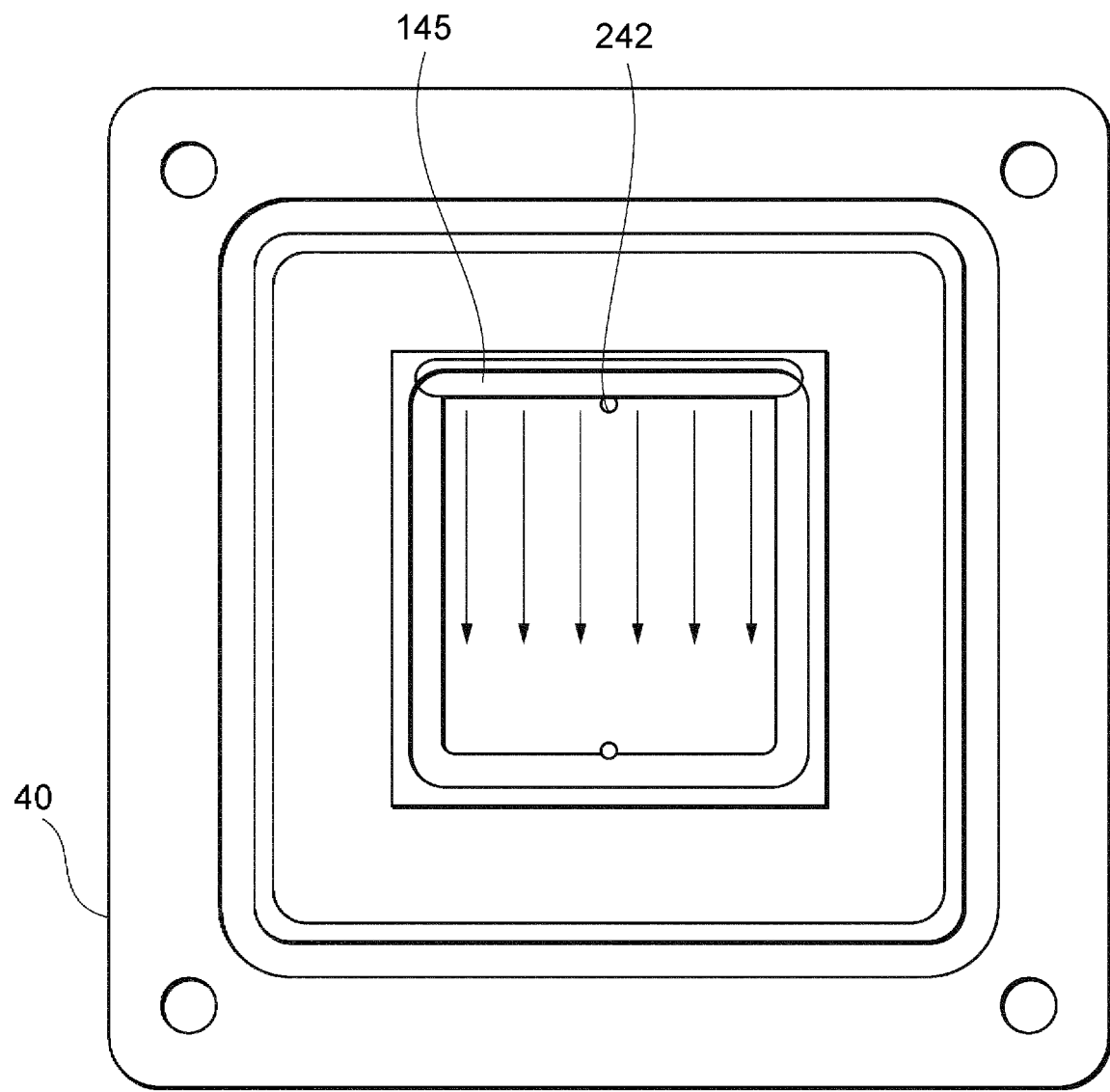
FIG. 5 is a front view of a part of a cell culture equipment according to an embodiment.

Alternatively, as shown in FIG. 4, one or more discharge ports 241 communicating with the inlet 240 shown in FIG. 3 may be provided in the inner wall of the medium holding vessel 40. The plurality of the discharge ports 241 shown in FIG. 4 are provided in a horizontal row for example. In terms of the number and sequence of the plurality of the discharge ports 241, they may be distributed either uniformly or randomly. The number and sequence of the plurality of the discharge ports 241 are set according to the viscosity and other properties of the medium. As shown in FIG. 5, by discharging the medium through the plurality of the discharge ports 241 it is possible to improve the uniformity of the medium in contact with the culture component permeable member 10 in the medium holding vessel 40.

It may be possible to insert a discharge block 145 including one or more discharge ports 241 into the inner wall of the medium holding vessel 40. For example, a plurality of discharge blocks 145 having different patterns such as numbers and sequences of which may be prepared and used according to the properties of the medium and the cultured cells. The upper side relative to the gravity of the inner wall of the medium holding vessel 40 may be designed to curve or bend upward or downward. The lower side relative to the gravity of the inner wall of the medium holding vessel 40 may be designed to bend or curve upward or downward.

As shown in FIGS. 4 and 5, an opening 242 may be provided near the plurality of the discharge ports 241 on the inner wall of the medium holding vessel 40. As medium discharged from the plurality of the discharge ports 241 is stored in the medium holding vessel 40, the air inside the medium holding vessel 40 is vented to the outside through the opening 242. After the medium has been added to the medium holding vessel 40, the opening 242 may be sealed.

As shown in FIG. 3, the inlet 240 and outlet 340 of the medium holding vessel 40 may be connected to the medium conduit 200, and medium may circulate between the medium holding vessel 40 and the medium conduit 200. The medium conduit 200 may include a resin tube or silicon tube or the like. The medium conduit 200 may be enveloped in a gas impermeable substance. In other words, the medium conduit 200 may be embedded in a gas impermeable substance. For example, the medium conduit 200 may be a hole provided in a member made of resin, glass, metal or the like. In this case, for example the medium conduit 200 is formed by sticking together members provided with convex parts. The medium conduit 200 may be provided with fluid machines for introducing medium into the medium holding vessel 40 and discharging medium from the medium holding vessel 40. The fluid machines include an introduction fluid machine 51 for introducing medium into the medium holding vessel 40 and a discharge fluid machine 52 for discharging medium from the medium holding vessel 40.

Positive displacement pumps may be used as the introduction fluid machine 51 and the discharge fluid machine 52 shown in FIG. 1. Examples of positive displacements pumps include reciprocating pumps such as piston pumps, plunger pumps and diaphragm pumps, as well as rotary pumps such as gear pumps, vane pumps and screw pumps. Examples of diaphragm pumps include tubing pumps and piezo pumps. Tubing pumps can be referred to peristaltic pumps. It is also possible to use a microfluidic chip module that combines a plurality of types of pumps.

By using a sealed pump such as a Perista pump (registered trademark), tubing pump or diaphragm pump, it is possible to transport liquid without the pump contacting the medium inside the medium conduit 200 shown in FIG. 3. Syringe pumps may be used for the introduction fluid machine 51 and discharge fluid machine 52. Even using a pump other than a sealed pump, it is possible to reuse it after heat sterilization treatment.

When the introduction fluid machine 51 is a sealed pump, the introduction fluid machine 51 includes a pump head 151 and a driver 251 such as a motor as shown in FIG. 1. The pump head 151 and the driver 251 are detachable. The pump head 151 is provided with a roller that squeezes a medium conduit such as a tube from the outside. The driver 251 rotates the roller of the pump head 151. When the discharge fluid machine 52 is a sealed pump, the discharge fluid machine 52 includes a pump head 152 and a driver 252 such as a motor. The pump head 152 and the driver 252 are detachable. The pump head 152 includes a roller that squeezes a medium conduit such as a tube from the outside. The driver 252 rotates the roller of the pump head 152.

As shown in FIG. 3, the medium conduit 200 may be provided with a medium tank 60 into which medium can enter. Medium entering the medium tank 60 from the medium conduit 200 then flows out again through the medium conduit 200. The volume of the medium circulating between the medium conduit 200 and the medium holding vessel 40 can be increased by providing a medium tank 60.

Figure 6:
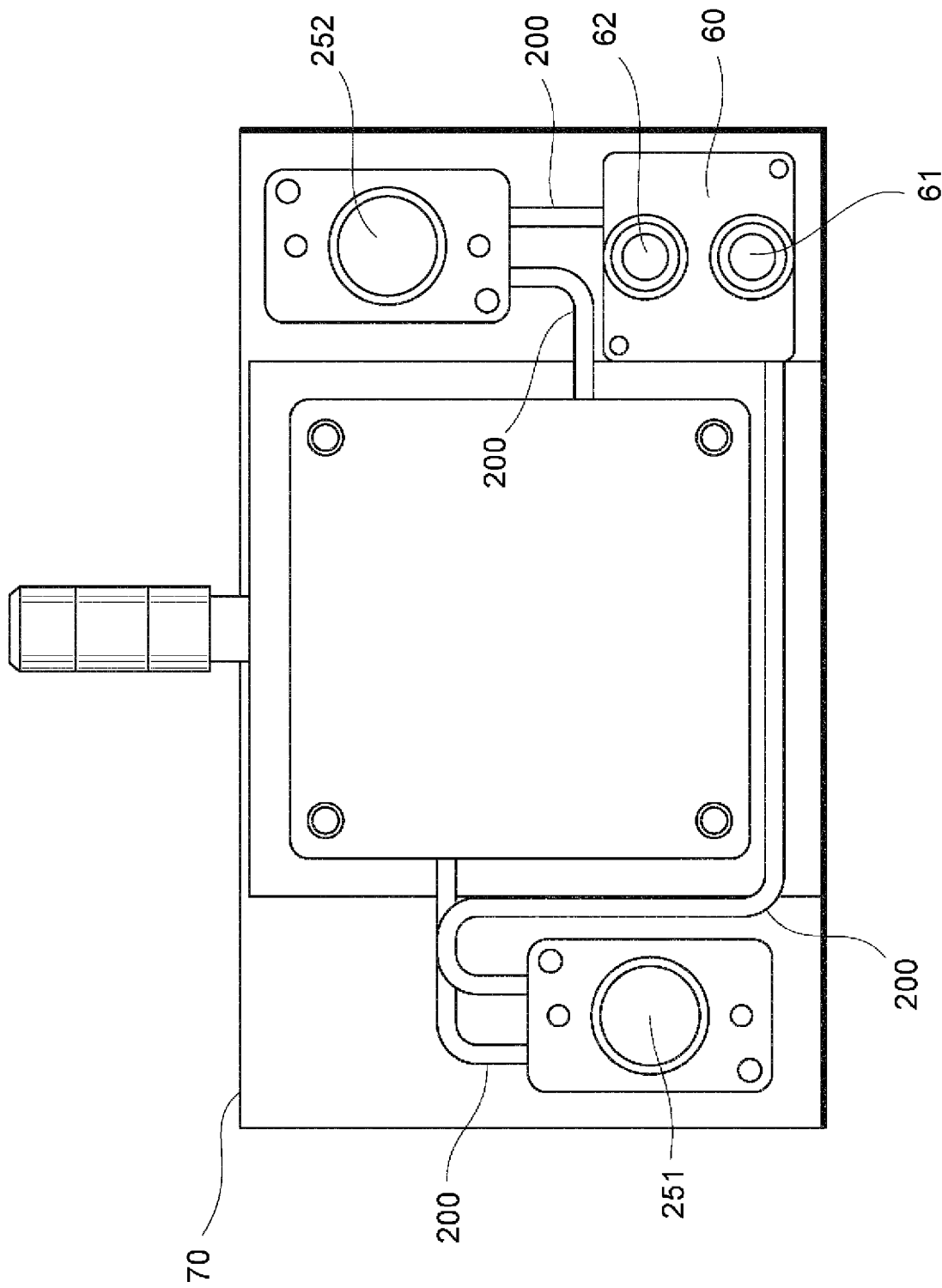
FIG. 6 is a rear view of a cell culture equipment according to an embodiment.

The medium tank 60 may include a supply inlet for supplying fluid to the inside of the medium tank 60 and an outlet for discharging fluid from the inside of the medium tank 60. For example, the plug 61 shown in FIG. 6, which can be connected to a supply equipment such as a bag, bellows or syringe for supplying fluid, is inserted into the supply inlet of the medium tank 60. The supply equipment may be fluid machine such as a pump. However, the supply equipment can be connected directly to the supply inlet of the medium tank 60. When the supply equipment is detachable from the supply inlet and the supply equipment is not connected to the supply inlet, the supply inlet can be sealed so that there is no fluid exchange between the inside and outside of the medium conduit 200 through the supply inlet. Alternatively, the supply inlet is shielded from the outside by connecting the supply equipment. The plug 61 may be a needleless connector. The needleless connector may be a split septum type or mechanical bulb type connector. When the supply equipment or a conduit connected to the supply equipment is inserted into the plug 61, no outside air penetrates the inside of the medium tank 60 through the plug 61. However, the plug 61 can be a connector into which a needle is inserted.

Also, for example a plug 62 that can be connected to a discharge equipment such as a bag, bellows or syringe for discharging the fluid inside the medium tank 60 is inserted into the outlet of the medium tank 60. The discharge equipment may be a fluid machine such as a pump. However, the discharge equipment can be connected directly to the outlet of the medium tank 60. The discharge equipment may actively aspirate the fluid in the medium conduit. Alternatively, the internal capacity of the discharge equipment may increase passively according to the pressure inside the medium conduit, causing the discharge equipment to receive fluid expelled from the medium conduit. When the discharge equipment is detachable from the outlet and the discharge equipment is not connected to the outlet, the outlet can be sealed so that there is not exchange of fluid between the inside and outside of the medium conduit 200 through the outlet. Alternatively, the outlet may be shielded from the outside by connecting it to the discharge equipment. The plug 62 may be a needleless connector. The needleless connector may be a split septum type or mechanical bulb type connector. When a discharge equipment or a conduit connected to a discharge equipment is inserted into the plug 62, outside air does not penetrate the inside of the medium tank 60 through the plug 62. However, the plug 62 can be a connector into which a needle is inserted.

For example, when the medium holding vessel 40 is in close contact with the culture vessel 30 through the inserted medium-side plate 22, the inserted culture component permeable member 10 and the inserted culture-side plate 21 as shown in FIG. 1 and the medium holding vessel 40, the medium conduit 200 and the medium tank 60 shown in FIG. 3 contain air, medium can be made to enter the medium holding vessel 40, the medium conduit 200 and the medium tank 60 by discharging the air in the medium holding vessel 40, the medium conduit 200 and the medium tank 60 from the outlet of the medium tank 60 while injecting medium into the medium holding vessel 40, the medium conduit 200 and the medium tank 60 from the supply inlet of the medium tank 60. The air layers inside the medium holding vessel 40, the medium conduit 200 and the medium tank 60 may be completely eliminated, or air layers may remain.

A supply equipment full of medium and an empty discharge equipment may be connected to the medium conduit 200, and the fluid machines may be driven to introduce medium into the medium conduit 200 from the supply equipment and introduce air into the discharge equipment. In this process, the supply equipment may actively inject medium into the medium conduit 200. Alternatively, medium from the supply equipment may be aspirated into the medium conduit 200, which is at low pressure due to the drive of the fluid machine and the internal volume of the supply equipment is passively reduced. Furthermore, the discharge equipment may actively aspirate the air in the medium conduit 200. Alternatively, air may flow into the discharge equipment from the inside of the medium conduit 200, which is at high pressure due to the drive of the fluid machine and the internal volume of the discharge equipment is passively increased.

In the case where the medium holding vessel 40, the medium conduit 200 and the medium tank 60 already contain medium, the cell medium in the medium tank 60 can be replaced by injecting medium into the medium tank 60 through the supply inlet of the medium tank 60 while discharging the medium already in the medium tank 60 through the outlet of the medium tank 60.

A supply equipment full of medium and an empty discharge equipment may be connected to the medium conduit 200, and the fluid machines may be driven to introduce new medium into the medium conduit 200 from the supply equipment and introduce old medium into the discharge equipment. In this process, the supply equipment may actively inject the new medium into the medium conduit 200. Alternatively, new medium from inside the supply equipment may be aspirated into the medium conduit 200, which is at low pressure due to the drive of the fluid machine and the internal volume of the supply equipment is passively reduced. Furthermore, the discharge equipment may actively aspirated the old medium in the medium conduit 200. Alternatively, old medium may flow into the discharge equipment from the inside of the medium conduit 200, which is at high pressure due to the drive of the fluid machine and the internal volume of the discharge equipment is passively increased.

The supply inlets for supplying medium to the medium conduit 200 and the medium holding vessel 40 and the outlets for discharging air from inside the medium conduit 200 and the medium holding vessel 40 may be located outside the part having the medium tank 60 in the medium conduit 200. For example, the supply inlets for supplying medium to the medium conduit 200 and the medium holding vessel 40 and the outlets for discharging air from inside the medium conduit 200 and the medium holding vessel 40 may be provided in the medium conduit 200.

The cell culture equipment according to the embodiment may include a temperature regulator for heating and cooling at least any one of the medium holding vessel 40, the medium conduit 200 and the medium tank 60. The medium temperature can be regulated by using the temperature regulator to adjust the temperature of any one of the medium holding vessel 40, the medium conduit 200 and the medium tank 60. The incubator according to the embodiment may be provided with a thermometer for measuring the temperature of the medium. The thermometer may measure the temperature of the medium based on the temperature of at least any one of the medium holding vessel 40, the medium conduit 200 and the medium tank 60, or may measure the temperature of the medium directly in contact with the medium. In this case, the temperature regulator may be subjected to feedback control so that the temperature of the medium is maintained at a predetermined temperature. The temperature of the medium is regulated at from 4° C. to 45° C., or from 20° C. to 45° C.

As shown in FIG. 3, the medium holding vessel 40, the medium conduit 200, the pump head 151, the pump head 152 and the medium tank 60 may be housed in a conduit case 70. In the conduit case 70, the medium holding vessel 40, the medium conduit 200, the pump head 151, the pump head 152 and the medium tank 60 may be completely embedded in a gas impermeable substance. The medium conduit 200 may be provided in the form of a tunnel in the gas impermeable substance. For example, the conduit case 70 is provided with a hole for inserting a shaft into the pump head 151, a hole for inserting a shaft into the pump head 152, a hole for inserting the plug 61 into the supply inlet of the medium tank 60, and a hole for inserting the plug 62 into the outlet of the medium tank 60. The hole for inserting the plug 61 into the supply inlet of the medium tank 60 and the hole for inserting the plug 62 into the outlet of the medium tank 60 may be closable.

Figure 7:
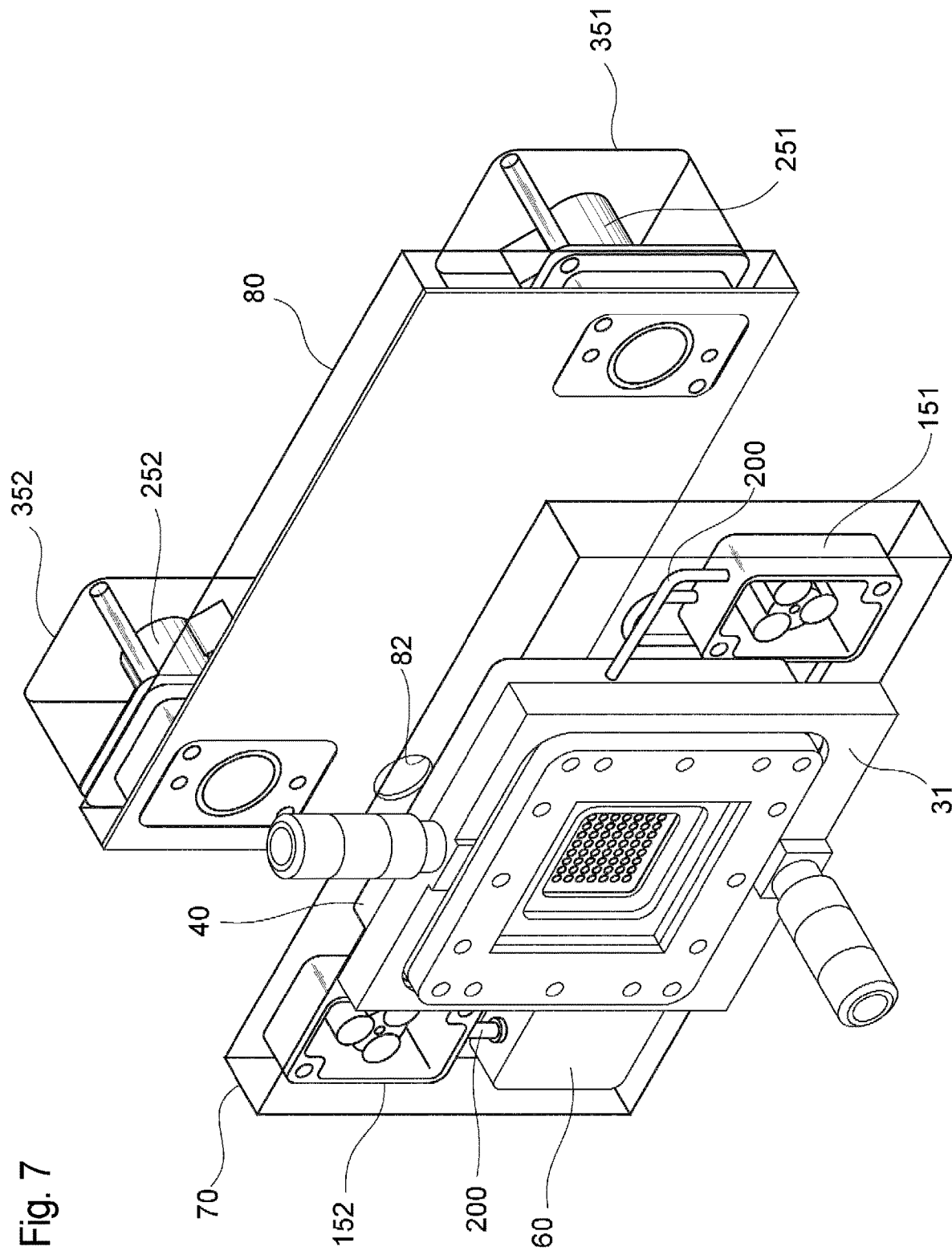
FIG. 7 is an exploded perspective view of a cell culture equipment according to an embodiment.

As shown in FIG. 7, the driver 251 of the introduction fluid machine 51 and the driver 252 of the discharge fluid machine 52 may be disposed on a substrate-like driver holding member 80. The driver holding member 80 is provided with a hole for inserting the plug 61 into the supply inlet of the medium tank 60 and a hole 82 for inserting the plug 62 into the outlet of the medium tank 60. The hole for inserting the plug 61 into the supply inlet of the medium tank 60 and the hole 82 for inserting the plug 62 into the outlet of the medium tank 60 may be closable.

The driver holding member 80 is brought into close contact with the conduit case 70 with the packing 90 shown in FIG. 1 in between. The packing 90 suppresses intrusion of air into the conduit case 70 from the area of contact between the conduit case 70 and the driver holding member 80.

The fluid machines for introducing medium into the medium holding vessel 40 and discharging medium from the medium holding vessel 40 may be covered by an outside air shielding member for the fluid machines. As shown in FIG. 7, the outside air shielding member for the fluid machines include for example an outside air shielding member for the introduction fluid machine 351 that covers the driver 251 of the introduction fluid machine 51 on the driver holding member 80, and an outside air shielding member for the discharge fluid machine 352 that covers the driver 252 of the discharge fluid machine 52 on the driver holding member 80.

The conduit case 70 and the driver holding member 80 are detachable. When the driver holding member 80 and the conduit case 70 are brought into close contact, the hole for inserting the plug 61 into the supply inlet of the medium tank 60 and the hole for inserting the plug 62 into the outlet of the medium tank 60 are closed, the driver 251 of the introduction fluid machine 51 is covered by the outside air shielding member for the introduction fluid machine 351 and the driver 252 of the discharge fluid machine 52 is covered by the outside air shielding member for the discharge fluid machine 352, the inside of the conduit case 70 is shielded from outside air and outside air can no longer penetrate the inside of the conduit case 70. As a result, there is no longer any exchange of gas between the inside and outside of the conduit case 70. Therefore, outside air no longer penetrates the medium holding vessel 40 and medium conduit 200. The conduit case 70 constitutes at least part of an outside air shielding member for the medium conduits, and by shielding this conduit case 70 from outside air, it is possible to suppress fluctuations in the pH of the medium inside the medium holding vessel 40 and the medium conduit 200 and maintain the pH within a predetermined range even if the medium conduit 200 is a gas permeable tube. The predetermined range of the medium pH is from 6.0 to 9.0 for example. Based on the inventors' findings, as the cells can be cultured in a completely shielded enclosed space, it is not necessary to actively supply carbon dioxide gas, nitrogen gas, oxygen gas or the like to the inside of the medium holding vessel 40 and medium conduit 200. Accordingly, it is not necessary to dispose the medium holding vessel 40 or the medium conduit 200 inside a $CO_2$ incubator. Furthermore, the cleanliness inside the medium holding vessel 40 and the medium conduit 200 is maintained as no cells, microorganisms, viruses or dust from outside the medium holding vessel 40 and the medium conduit 200 can penetrate the insides of the sealed medium holding vessel 40 and the medium conduit 200. Therefore, it is not necessary to dispose the medium holding vessel 40 and the medium conduit 200 in a clean room. The medium holding vessel 40 may be enveloped in a gas impermeable substance. In other words, the medium holding vessel 40 may be embedded in a gas impermeable substance.

When the driver holding member 80 is removed from the conduit case 70, the hole in the conduit case 70 for inserting the plug 61 in the supply inlet of the medium tank 60 and the hole in the conduit case 70 for inserting the plug 62 in the outlet of the medium tank 60 can be blocked to thereby seal the conduit case 70 and prevent substances inside the conduit case 70 from escaping outside while preventing outside air from penetrating the inside of the conduit case 70.

The conduit case 70 containing the medium conduit 200 and the pump heads 151, 152 is disposable. On the other hand, the driver holding member 80 holding the drivers 251 and 252 is reusable.

For example, the introduction fluid machine 51 and the discharge fluid machine 52 are controlled so that the amount of medium transported into the medium holding vessel 40 by the introduction fluid machine 51 shown in FIG. 2 is the same as the amount of medium discharged from the medium holding vessel 40 by the discharge fluid machine 52. The introduction fluid machine 51 and the discharge fluid machine 52 may constantly transport medium inside the medium holding vessel 40, or they may transport the medium at appropriate intervals.

When medium is transported constantly into the medium holding vessel 40, the flow volume of the medium transported into the medium holding vessel 40 may or may not be constant. For example, the medium and the cell colonies in the medium can be observed with an imaging apparatus, and the flow volume of the medium transported into the medium holding vessel 40 can be increased or reduced depending on the condition of the medium and the cell colonies in the medium.

Instead of medium being transported constantly into the medium holding vessel 40, medium transport may be initiated and ended based on changes in the condition of the medium, the condition of the cell colonies in the medium, the number of cells, the number of cell colonies, and the turbidity and pH of the medium. In this case, the flow volume of the transported medium can also be increased or decreased depending on the condition of the medium and the cell colonies in the medium.

Cells may collide and bind randomly in the medium to form cell clumps (colonies) of various sizes as the medium is stirred. The homogeneity of the colonies may not be maintained as a result. Moreover, nutrients and growth factors may not reach the interior of colonies that are too large, and differentiation and cell death may occur in the interior of these colonies. On the other hand, colonies that are too small may not be suited to passage culture. However, in the culture vessel 30 shown in FIG. 2 the frequency of collisions between cells is low because the medium flows slowly or does not flow at all. Therefore, clonality can be maintained in the colonies. Thus, when the cells are stem cells such as iPS cells for example, it is possible to ensure the clonality of stem cells derived from one somatic cell. In addition, as the frequency of collisions between stem cells is low, the size of the stem cell colonies can be kept uniform.

The cell culture equipment according to the embodiment may include an imaging apparatus such as a photographic camera or video camera that images the cell-containing medium in the culture vessel 30 through the window 132 in the cover 32 of the culture vessel 30. By using a colorless medium, it is possible to suppress diffuse reflection and autofluorescence that may occur if colored medium is used. However, a pH indicator such as phenol red may be included for purposes of confirming the pH of the medium. As stem cells that remain undifferentiated have different cell shapes, sizes and the like from differentiated cells, the cell culture equipment may be provided with a differentiation state monitoring device that monitors the differentiation states of the cells by imaging the cells inside the culture vessel 30.

In the case where cells are cultured on a flat dish such as a petri dish, an existing region of the cells spreads in a plane. Thus, almost all of the cells can be in focus if the imaging apparatus and the petri dish are disposed so that the optical axis of the lens of the imaging apparatus is perpendicular to the plane of the petri dish.

However, in the case where the cells inside the culture vessel 30 are floated in a medium to perform suspension culture, the existing region of the cells spreads in three dimensions, and there is variation in the distance between the imaging apparatus and the individual cells in the direction of the optical axis. It can thus be difficult to focus all of the cells at the same time.

However, a deeper depth of field can be obtained using a bright lens (a lens with a small F value) or by constricting the lens aperture as much as possible while exposing the object of measurement to a bright light.

Alternatively, an image with an artificially deep focus can be obtained by taking a plurality of images while changing the focal position of the lens bit by bit, and then combining a plurality of the captured images. Furthermore, each of the plurality of the images contains a mixture of cells in focus and blurred out-of-focus cells. Therefore, partial in-focus images can be collected from the plurality of the images and used to produce a single composite image.

The cells may be imaged through a telecentric lens for example. With a telecentric lens, the principal rays passing through the center of the lens aperture from the cells or other photographic objects are made parallel to the optical axis of the lens, so that the size of the imaged cells does not change with distance even if the distance from the imaging apparatus to each of the plurality of the cells in the culture vessel 30 is not uniform.

A scattered light illumination method in which the light source for illumination is disposed in a direction perpendicular to the optical axis of the imaging apparatus or in a direction close to the imaging apparatus from the perpendicular direction, and the cells in the culture vessel 30 are exposed to light from this illumination light source, may be used in the case where imaging cells inside the culture vessel 30 with the imaging apparatus. Scattered light from the illumination light achieving the cells thus reaches the imaging apparatus, while scattered light that does not achieve the cells does not reach the imaging apparatus. The medium in the images thus appear relatively dark, and the cells appear relatively light. However, the illumination method is not limited to this as long as cells can be confirmed in the images.

Figure 8:
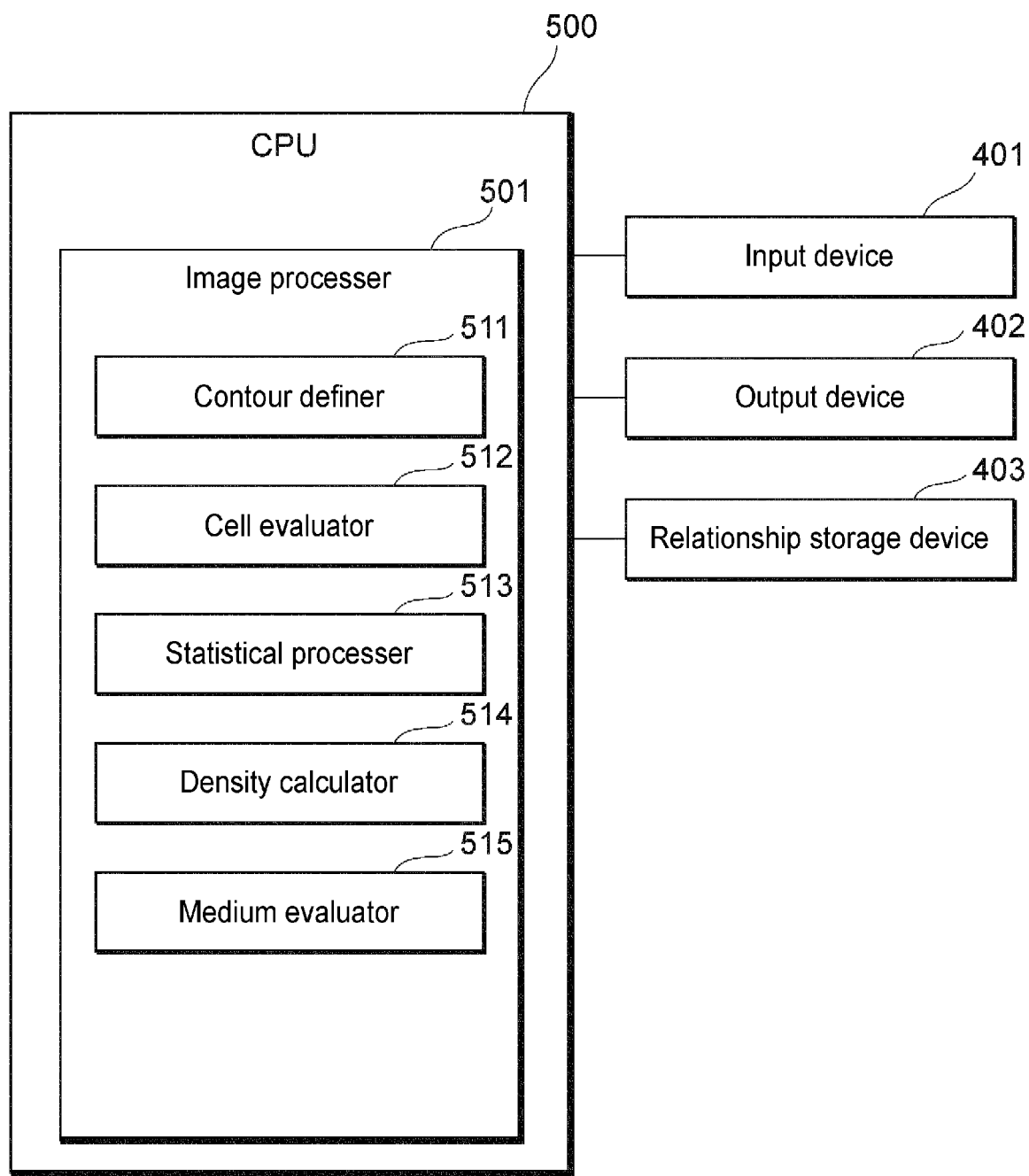
FIG. 8 is a model view of a computer according to an embodiment.

As shown in FIG. 8, the cell culture equipment according to the embodiment may include a central processing unit (CPU) 500 including an image processor 501 for processing images imaged by the imaging apparatus in front of the culture vessel 30. An input device 401 such as a keyboard or mouse and an output device 402 such as a monitor may be connected to the CPU 500. The CPU 500 receives images from the imaging apparatus disposed in front of the culture vessel 30 shown in FIG. 2 through a bus, image interface and the like.

Figure 9:
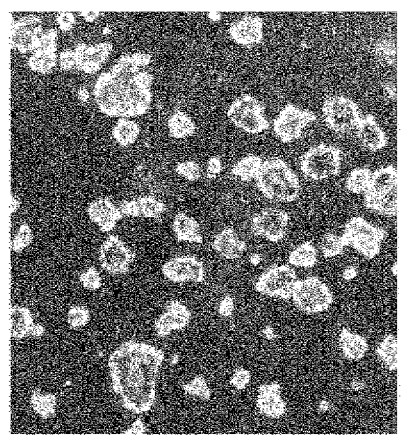
FIG. 9 is an example of an image of a cell colony in an embodiment.

The image processer 501 shown in FIG. 8 may include a contour definer 511 for defining the contours of the cells or cell colonies. FIG. 9 shows one example of an image of an iPS cell colony enlarged and imaged through a macro zoom lens. In the image shown in FIG. 9, the parts appearing as white clumps are iPS cell colonies, while the dark parts of the image represent medium.

Figure 10:
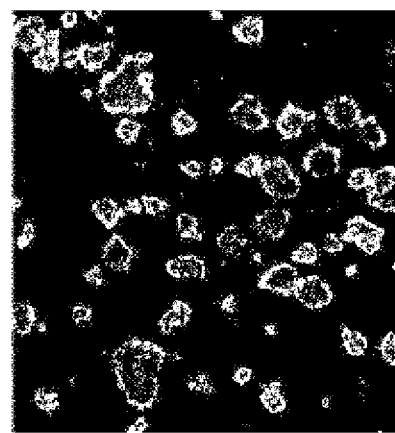
FIG. 10 is an example of an image of a binarized cell colony in an embodiment.

Assuming that the image shown in FIG. 9 is an 8-bit gray scale image, if the image is binarized by converting the brightness values of pixels with brightness values at or above a predetermined threshold to a maximum brightness value of 255 for example and the brightness values of pixels with brightness values below a predetermined threshold to a minimum brightness of value of 0 for example, not only the areas of the medium but also the interiors of the cells or cell colonies appear with the minimum brightness (black) as shown in FIG. 10, and the interiors of the cells or cell colonies and the areas of medium may appear linked together. For this reason, it may not always be possible to extract cells or cell colonies by binarization processing.

Figure 11:
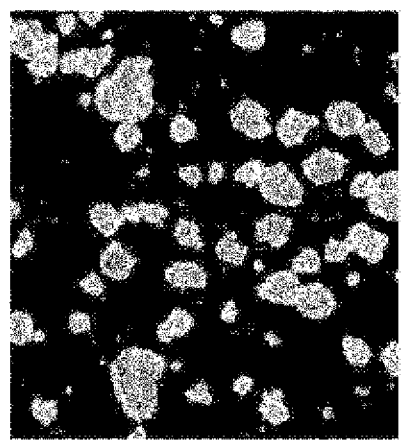
FIG. 11 is an example of an image of a cell colony to which a high-pass filter has been applied in an embodiment.

However, the contour definer 511 shown in FIG. 8 applies a high-pass filter to the cell images whereby high frequency components at or above a predetermined frequency in the spatial frequency are passed while low frequency components below the predetermined frequency are blocked, and the brightness value is set to a minimum value such as 0. In the cell images, the spatial frequency in the parts with cells or cell colonies contains many high frequency components, while the spatial frequency in the parts with medium contains few high frequency components. Therefore, as shown in FIG. 11, the brightness value of the parts with medium becomes a minimum value such as 0 in the cell images to which the high-pass filter has been applied, while in the parts with cells or cell colonies, the brightness value becomes a relatively high value in comparison to the parts with medium. Therefore, areas in which the brightness value is not the minimum value can be identified as cells or cell colonies.

In the image shown in FIG. 11, even if the areas where the brightness value is not the minimum value are detected as blobs by blob analysis, for example two adjacent cells or cell colonies may still be identified as one cell or cell colony.

However, the contour definer 511 shown in FIG. 8 applies a watershed algorithm to images that have passed through the high-pass filter. The watershed algorithm views the brightness gradient of the image as an undulating mountain range, and divides the images into sections with one section being a region created by water flowing from the high part of the mountains (where the brightness value is high or where the brightness value is low) to the low part of the mountains (where the brightness value is low or where the brightness value is high).

Figure 12:
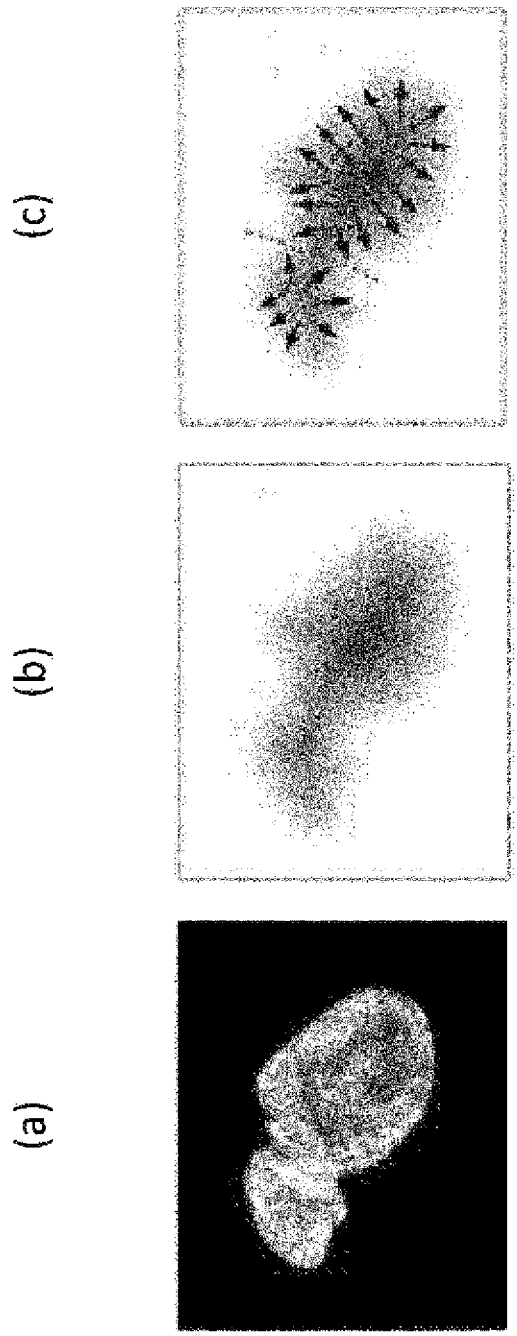
FIG. 12 is an example of an image of a cell colony to which a watershed algorithm has been applied in an embodiment.

For example, before applying the watershed algorithm to an image, the contour definer 511 converts the image by the distance transform method. The distance transform method is an image conversion method whereby the brightness value of each pixel of an image is converted based on the distance to the nearest background pixel. For example, as shown in FIG. 12(a), in an image that has passed through the high-pass filter the brightness value of the region of medium is converted all at once to the maximum brightness value of 255, becoming the white background shown in FIG. 12(b). Furthermore, the brightness value of each pixel within the cell region is converted to a value between 0 and less than 255 according to the distance to the nearest background pixel. For example, the brightness value is lower the greater the distance to the nearest background pixel.

Next, the contour definer 511 applies the watershed algorithm to the image that has been converted by the distance transform method. In the image shown in FIG. 12(b), the dark parts with low brightness are regarded as mountain ridges, the flow of water when water is dropped from vertically above the image is estimated as shown by the arrows in FIG. 12(c), the areas where the water flowing from various directions collides are regarded as valleys as shown the broken line in FIG. 12(c), and the cell regions are divided at the bottoms of the valleys.

Figure 13:
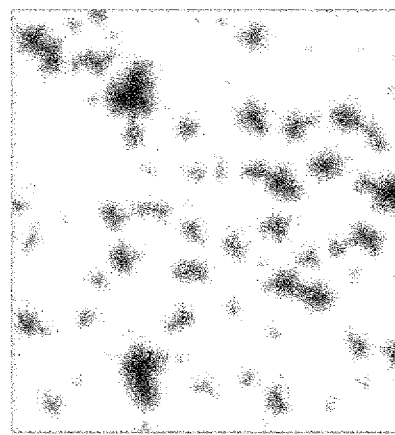
FIG. 13 is an example of an image of a cell colony to which the distance transform method has been applied in an embodiment.
Figure 14:
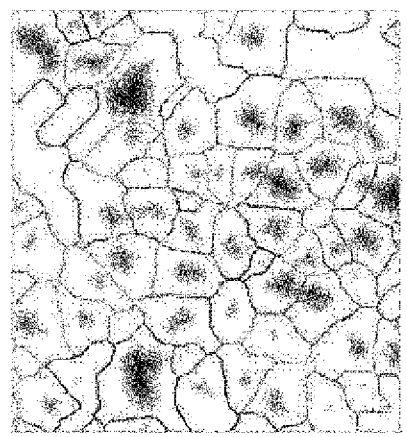
FIG. 14 is an example of an image of a cell colony to which a watershed algorithm has been applied in an embodiment.
Figure 15:
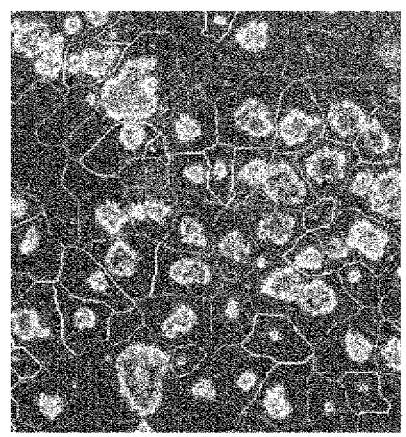
FIG. 15 is an example of an image of a cell colony that has been divided into a plurality of sections in an environment.
Figure 16:
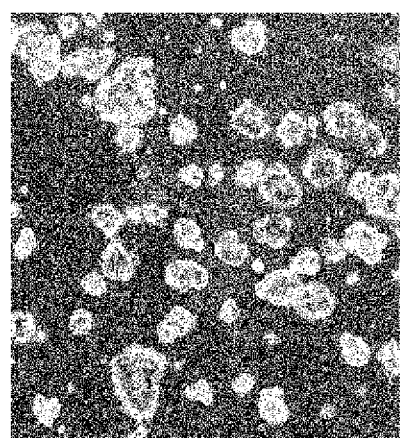
FIG. 16 is an example of an image of a cell colony whose contour has been extracted in an embodiment.

When the pixels of the cell regions in the image shown in FIG. 11 are converted by the distance transform method, the image shown in FIG. 13 is obtained. When the watershed algorithm is applied to the image shown in FIG. 13, the image shown in FIG. 14 is obtained. When the resulting dividing lines are overlaid over the original image shown in FIG. 9, the image shown in FIG. 15 is obtained. In FIG. 15, the cells or cell colonies in each of the regions delineated by the dividing lines can be considered as single cells or cell colonies rather than a plurality of adjacent cells or cell colonies. Consequently, a single cell or cell colony can be accurately extracted by extracting the contour of the cell or cell colony as shown in FIG. 16.

The image processer 501 shown in FIG. 8 may include a cell evaluator 512. The cell evaluator 512 evaluates the size and the like of single cells or cell colonies extracted by the contour definer 511. For example, the cell evaluator 512 calculates the area of a single cell or cell colony extracted by the contour definer 511. Moreover, for example when a single cell or cell colony seems to be roughly circular in shape, the cell evaluator 512 uses the following formula (1) to calculate the diameter of the single cell or cell colony from the area:

$$D=2(s/n)^{1/2} \tag{1}$$

where D is the diameter and S is the area.

If a cell colony grows too large, the nutrients and hormones contained in the medium cannot penetrate the interior of the colony, and the cells may differentiate. If cells are incubated when a cell colony is too small, on the other hand, cell death and karyotype abnormalities may occur.

Consequently, the cell evaluator 512 may issue a warning in the case where the size of an individual cell colony is outside the appropriate range. In the case where the size of an individual cell colony reaches a predetermined threshold, the cell evaluator 512 may output that it is time for passage culture. The fluid machines of the cell culture equipment may be controlled to change the circulation rate of the medium in the medium conduit based on the calculated size of the cell colonies. For example, the medium circulation rate may be raised as the cell colonies grow larger.

The image processer 501 may include a statistical processer 513 for statistically processing data obtained from image-processed images. The statistical processer 513 may for example calculate the frequency distribution of size or prepare histograms for cell colonies extracted by the contour definer 511. The statistical processer 513 may obtain data about cells continuously and regularly to calculate the growth, numbers, density and the like of the cell colonies. It is thus possible to quantitatively assess the condition of the cell colonies and stabilize the culture results. The fluid machines of the cell culture equipment can also be controlled to change the circulation rate of the medium in the medium conduit depending on the calculated number of cell colonies. For example, the circulation rate of the medium can be raised as the number of cell colonies increases.

The image processor 501 may include a density calculator 514 that calculates the turbidity of the medium from images of the medium and calculates the density of the cells or cell colonies in the medium based on the turbidity of the medium.

For example, a relationship storage 403 including a volatile memory, non-volatile memory or the like is connected to the CPU 500. The relationship storage 403 stores for example a previously determined relationship between the turbidity of a medium and the density of cells or cell colonies in the medium. The density calculator 514 reads out the relationship between the turbidity and the density from the relationship storage unit 403. The density calculator 514 then calculates the density of the cells or cell colonies in the medium based on a medium density value calculated from an image of the medium and the stored relationship between turbidity and density. It is thus possible to measure the density of the cells or cell colonies in the culture vessel 30 non-invasively without harvesting cell colonies from the medium. Instead of using medium turbidity, the density calculator 514 can also calculate the density value of the cells or cell colonies in the medium from the number of extracted cells and cell colonies and the ratio of the area volume actually imaged by the imaging apparatus relative to the volume of the culture vessel 30 as a whole.

In the case where the density of the cells or cell colonies reaches a predetermined threshold, the density calculator 514 may report that it is time for passage culture. The density calculator 514 can also calculate the density of the cells or cell colonies in the medium over time, and then calculate the cell colony growth rate. An abnormal growth rate may indicate that the cells are abnormal. For example, in the case where the density calculator 514 has calculated an abnormal growth rate, it issues a warning. In this case, cell culture may be stopped.

In the case where the density of the cells or cell colonies in the medium is too high or the cell colonies grow to closely together, a plurality of cells or cell colonies may adhere together to form one large cell colony. In large cell colonies, nutrients and hormones in the medium may not reach the interior of colonies, and cells in the interior may differentiate. In the case where the density of the cells or cell colonies in the medium is below the preferred range, on the other hand, the cell colony growth rate and cell colony forming ability may decline significantly.

With the density calculator 514, however, it is easy to judge whether the density of the cells or cell colonies is within the desired range as the density of the cells or cell colonies can be calculated. In the case where the density of the cells or cell colonies falls below the desired range, a decision may be made to stop culture for example. The fluid machines of the cell culture equipment can also be controlled to change the circulation rate of the medium in the medium conduit according to the calculated density of the cells or cell colonies. For example, the circulation rate of the medium can be raised as the density of the cells or cell colonies increases.

The image processer 501 may include a medium evaluator 515 for evaluating the medium based on images of the medium in which the cells are cultured inside the culture vessel 30 of the cell culture equipment. For example, the medium evaluator 515 subjects images of the medium to image processing and represents the color of the medium in terms of the three parameters of hue, saturation and value (HSV). Of these, hue is a parameter that generally corresponds to the concepts of "tint" or "color". Hue is generally represented in angle units.

For example, the relationship storage 403 stores a previously determined relationship between the hue of the medium and the pH of the medium. The medium evaluator 515 then reads the relationship between hue and pH from the relationship storage 403. The medium evaluator 515 further calculates a value for the pH of the imaged medium based on the hue value of the medium as calculated from images of the medium and the stored relationship between hue and pH. For example, the medium evaluator 515 may obtain images of the medium and calculate the pH value of the medium over time.

In the case where the hue of the medium or the pH of the medium in which cells are cultured in the culture vessel 30 shown in FIG. 2 falls outside a predetermined range, the medium evaluator 515 may decide to promote medium exchange with the medium stored in the medium holding vessel 40, or may judge that the medium has become contaminated. Medium exchange here includes replacing part of the medium or replenishing the medium.

The medium evaluator 515 shown in FIG. 8 may calculate the growth rate of the cells from the rate of change in the hue of the medium in which the cells are cultured in the culture vessel 30. For example, the relationship storage 403 stores a previously determined relationship between the rate of change in the hue of the medium and the growth rate of the cells. The medium evaluator 515 reads the stored relationship between the rate of change in hue and the growth rate from the relationship storage 403. The medium evaluator 515 then calculates a value for the growth rate of the cells from the calculated value of the rate of change in hue and the stored relationship between the rate of change in hue and the growth rate.

With the cell culture equipment of the embodiment, for example it is possible to reduce the risk of cross-contamination due to leakage of cells from the culture apparatus as the cells are cultured in a completely sealed system. For example, the risk of infection to the operator due to cell leakage can also be reduced even if the cells are contaminated with a virus such as the HIV or hepatitis virus. The risk that the medium in the cell culture equipment will be contaminated by bacteria, viruses, molds and the like in the air outside the cell culture equipment can also be reduced. Furthermore, with the cell culture equipment of the embodiment, cells can be cultured without using a $CO_2$ incubator.

The present invention was described above based on the embodiment, but the states and drawings that form part of the above Disclosures should not be understood as limiting the invention. Various embodiments, alternative embodiments and operational techniques should be obvious to those skilled in the art from these disclosures. For example, the medium conduit 200 does not need to be connected to the medium holding vessel 40 shown in FIG. 3 if the medium does not need to be circulated. Differentiated cells such as blood cells can also be reprogrammed into stem cells or differentiated cells such as nerve cells can be induced from stem cells in the culture vessel 30 of the cell culture equipment according to the embodiment. The cells in the culture vessel 30 may be cultured by suspension culture or by adhesion culture. If the cells are adhesion cultured, the surface of the culture-side plate 21 shown in FIG. 1 may be cell adhesive, or the surface of the culture component permeable member 10 may be cell adhesive. A medium conduit may be used without being connected to a medium holding vessel or culture vessel, and cells may be cultured in the medium conduit. In this case, the cells or medium being cultured in the medium conduit may be observed. Thus, the present invention should be understood to encompass various embodiments and the like that are not described here.

EXAMPLES

Example 1

Figure 17:
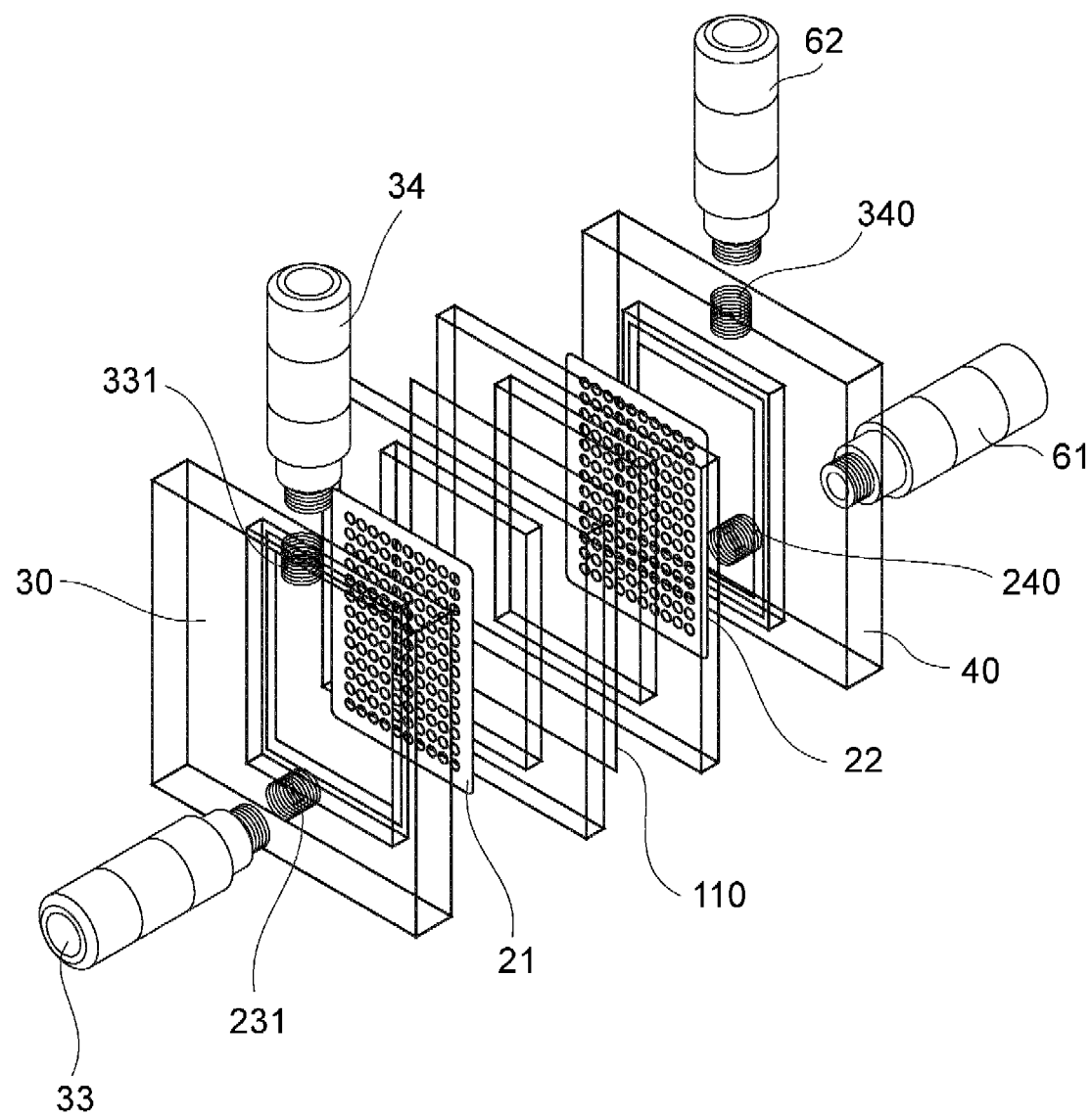
FIG. 17 is an exploded perspective view of the cell culture equipment according to Example 1.
Figure 18:
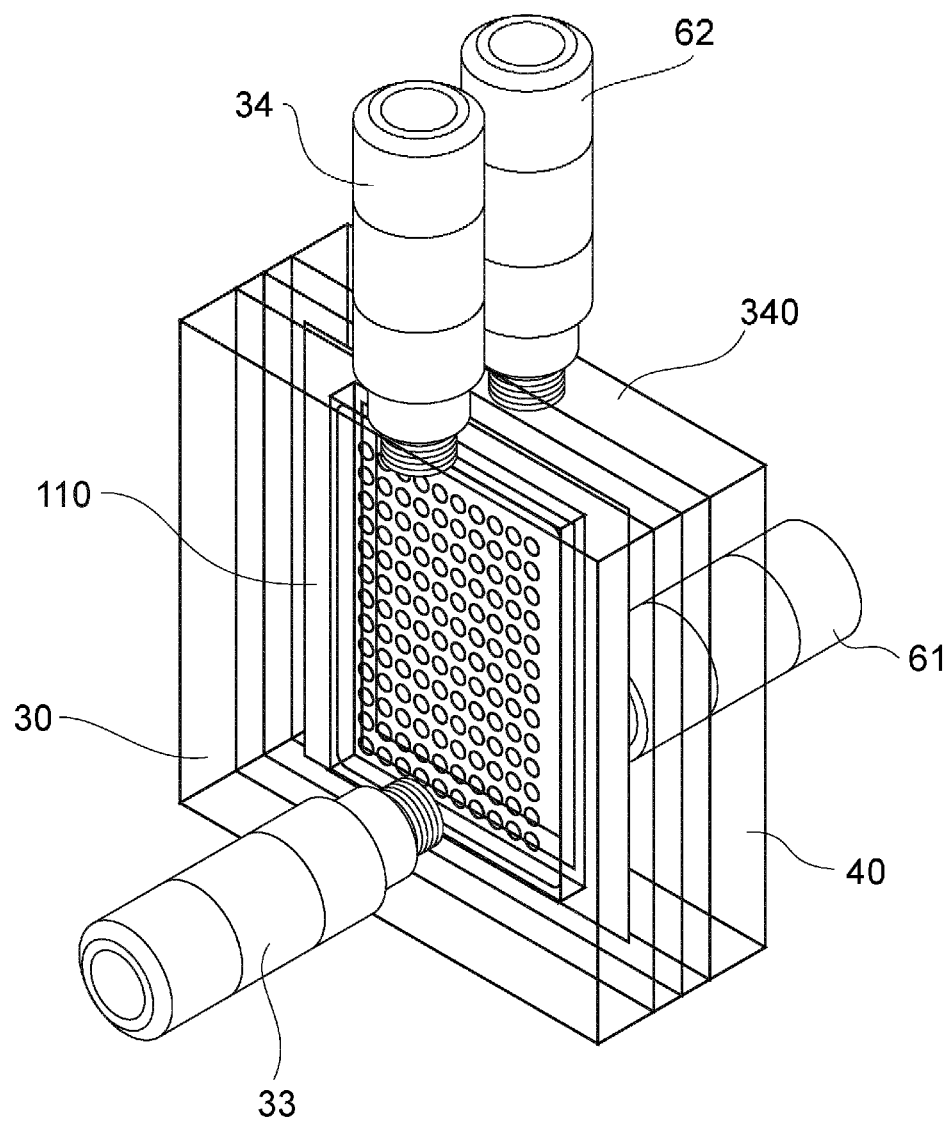
FIG. 18 is a perspective view of the cell culture equipment according to Example 1.

As shown in FIGS. 17 and 18, a semipermeable membrane 110 (Asahi Kasei Corp. or Spectrum) was sandwiched between a culture-side plate 21 and a medium-side plate 22, and the semipermeable membrane 110, the culture-side plate 21 and the medium-side plate 22 were further sandwiched between a culture vessel 30 and a medium holding vessel 40.

DMEM/F12 containing 20% replacement serum (Knock-Out SR, registered trademark, Gibco) was gelled to prepare a gel medium. $2 \times 10^5$/ml of iPS cells prepared as single cells were added to the gel medium to prepare a cell-containing medium.

The cell-containing medium was placed in a syringe, and the syringe was connected to the supply inlet 231 of the culture vessel 30 through the plug 33. An empty syringe was also connected to the outlet 331 of the culture vessel 30 through the plug 34. Next, the cell-containing culture in the syringe was injected into the culture vessel 30 through the supply inlet 231 of the culture vessel 30. The rise in pressure inside the culture vessel 30 caused the piston of the syringe connected to the outlet 331 to rise passively, and the air inside the culture vessel 30 moved to the syringe connected to the outlet 331 of the culture vessel 30. Cell-containing medium was injected into the culture vessel 30 until the air layer inside the culture vessel 30 was completely eliminated. The supply inlet 231 and the outlet 331 of the culture vessel 30 were then blocked.

Gel medium was placed in a syringe, and the syringe was connected to the inlet 240 of the medium holding vessel 40 through the plug 61. An empty syringe was also connected to the outlet 340 of the medium holding vessel 40 through the plug 62. Next, the gel medium in the syringe was injected into the medium holding vessel 40 through the inlet 240 of the medium holding vessel 40. The rise in pressure inside the medium holding vessel 40 caused the syringe connected to the outlet 340 of the medium holding vessel 40 to rise passively, and the air inside the medium holding vessel 40 moved to the inside of the syringe connected to the outlet 340 of the medium holding vessel 40. Gel medium was injected into the medium holding vessel 40 until the air layer inside the medium holding vessel 40 was completely eliminated. The inlet 240 and outlet 340 of the medium holding vessel 40 were then blocked. This served to seal the inside of the culture vessel 30 and the medium holding vessel 40, so that there was no gas exchange whatsoever between the inside and outside of the culture vessel 30 and medium holding vessel 40.

Suspension culture of iPS cells was initiated inside the culture vessel 30. Once every 2 days thereafter, 2 mL of new gel medium was substituted for 2 mL of gel medium inside the medium holding vessel 40. 7 to 10 days after the initiation of culture in the culture vessel 30, the cell-containing medium inside the culture vessel 30 was extracted with a syringe, and iPS cell colonies that had formed in the gel medium were collected with a filter, washed with PBS, and placed in a Falcon tube. 500 μL of a cell dissociation enzyme (TrypLE Select, Thermo Fisher) was further added to the cell colonies, which were then incubated for 5 minutes in a $CO_2$ incubator. The Falcon tube was then removed from the incubator, and 500 μL of cell medium was added to the Falcon tube to suspend the cell colonies and make the iPS cells into single cells. 2 mL of cell medium was added to the Falcon tube, which was then centrifuged at 200 g with a centrifuge. Following centrifugation, the supernatant in the Falcon tube was removed, and the iPS cells and gel medium were placed in a Falcon tube to prepare a cell-containing medium. The cell-containing medium was then injected into the culture vessel 30 as described above, and the iPS cells were suspension cultured for 7 to 10 days with 2 mL of gel medium substituted inside the medium holding vessel 40 once every 2 days.

Passage and 7- to 10-day suspension culture were subsequently repeated as described above, and the iPS cells were suspension cultured in the sealed culture vessel 30 for a total of at least one month.

Figure 19:
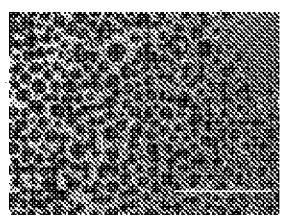
FIG. 19 is a microscopic photograph of a cell colony according to Example 1.

The iPS cells cultured in the culture vessel 30 were observed under a microscope, and formation of uniform cell colonies was confirmed as shown in FIG. 19.

When the cells were passaged, some of the single-cell iPS cells were dispensed, and fixed with 4% paraformaldehyde. The expressed amount of the cell surface antigen TRA-1-60 in the fixed iPS cells was then measured with a flow cytometer. TRA-1-60 is a surface antigen characteristic of pluripotent stem cells, and the expressed amount thereof is known to be reduced in differentiated cells.

Figure 20:
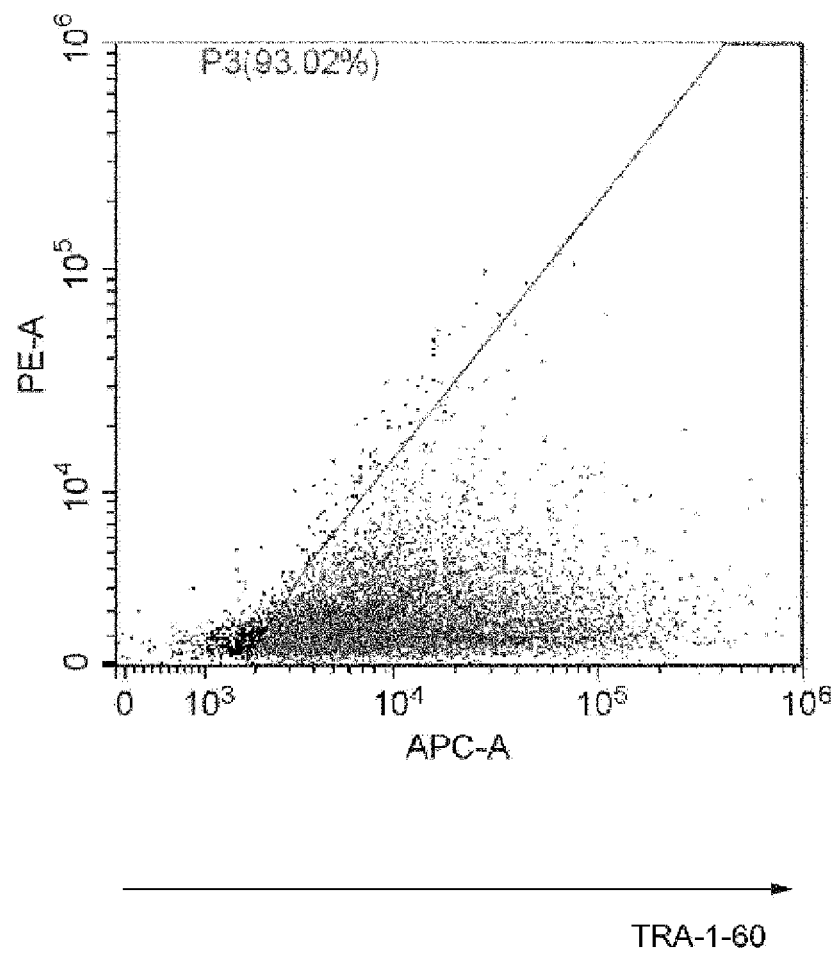
FIG. 20 is a histogram showing the results of flow cytometry of iPS cells according to Example 1.

As a result, as shown in FIG. 20, at least 90% of the iPS cells were TRA-1-60 positive on the 39th day after the start of culture. This shows that by sealing the container, it is possible to culture stem cells long-term in an undifferentiated and pluripotent state without controlling the carbon dioxide concentration inside the container.

Reference Example

A gel medium was prepared in the same manner as in Example 1. iPS cells that had been made into single cells were added to the gel medium. The gel medium containing the iPS cells was placed in a 15 mL Falcon tube. The cap of the Falcon tube was then tightened firmly.

The Falcon tube was set in an incubator with a carbon dioxide concentration of 5%, and suspension culture of the iPS cells was initiated. The cap of the Falcon tube was subsequently opened once every 2 days, and 2 ml of gel medium was added to the Falcon tube. The cap was tightened again as described above after the gel medium was added.

From 7 to 10 days after the initiation of culture in the Falcon tube, the cap of the Falcon tube was opened and iPS cell colonies that had formed in the gel medium were collected with a filter, washed with PBS, and placed in a Falcon tube. 500 μL of a cell dissociation enzyme was added to the cell colonies, which were then incubated for 5 minutes in a $CO_2$ incubator. The Falcon tube was then removed from the incubator, and 500 μL of stem cell medium was added to the Falcon tube to suspend the cell colonies and make the iPS cells into single cells. 2 mL of iPS medium was added to the Falcon tube, which was then centrifuged at 200 g with a centrifuge. After centrifugation, the supernatant in the Falcon tube was removed, and the iPS cells were placed in a Falcon tube together with a gel medium. The iPS cells were then suspension cultured in the sealed Falcon tube for 7 to 10 days with gel medium added once every two days as described above.

Passage and 7- to 10-day suspension culture were subsequently repeated as described above, and the iPS cells were suspension cultured in the sealed Falcon tube for a total of at least one month.

Figure 21:
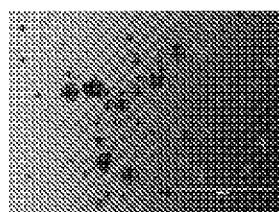
FIG. 21 is a microscopic photograph of a cell colony according to a reference example.
Figure 22:
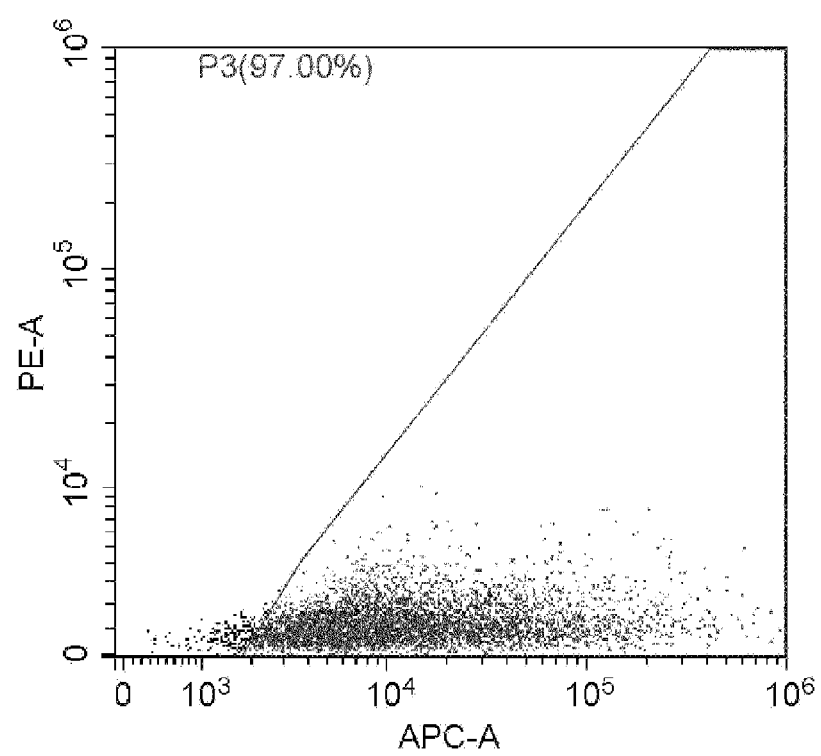
FIG. 22 is a histogram showing the results of flow cytometry of iPS cells according to a reference example.

When the iPS cells cultured in the Falcon tube were observed under a microscope, formation of cell colonies was confirmed in all cases as shown in FIG. 21. Moreover, when the expressed amount of the cell surface antigen TRA-1-60 in the iPS cells was measured with a flow cytometer in the same manner as Example 1, almost 100% of the iPS cells were TRA-1-60 positive as shown in FIG. 22. The sizes and numbers of the iPS cell colonies cultured in the Falcon tube were also measured with the results shown in FIG. 23.

Example 2

A cell-containing medium was prepared in the same manner as Example 1. A cell culture equipment similar to the cell culture equipment shown in FIG. 2 was also prepared. The cell-containing medium was injected into the culture vessel 30 until the air layer inside the culture vessel 30 was completely eliminated. The supply inlet and outlet of the culture vessel 30 were then blocked. The medium holding vessel 40, the medium conduit 200 and the medium tank 60 were filled with gel medium. The inlet and outlet of the medium tank 60 were then blocked. The insides of the culture vessel 30 and the medium holding vessel 40 were sealed so that there was no gas exchange whatsoever between the inside and outside of the culture vessel 30 and the medium holding vessel 40.

The gel medium was circulated inside the medium holding vessel 40, the medium conduit 200 and the medium tank 60, and suspension culture of iPS cells was initiated inside the culture vessel 30. Subsequently, 10 mL of the gel medium inside the medium tank 60 was replaced with 10 mL of new gel medium once every 2 to 6 days. 7 to 10 days after the beginning of culture in the culture vessel 30, the cell-containing medium inside the culture vessel 30 was extracted with a syringe and passaged in the same manner as Example 1, and cell-containing medium was injected into the culture vessel 30 as described above. 10 mL of the gel medium inside the medium tank 60 was replaced once every 4 days as the iPS cells were suspension cultured for 7 to 10 days.

Passage and 7- to 10-day suspension culture were subsequently repeated as described above, and the iPS cells were suspension cultured in the sealed culture vessel 30 for a total of at least one month.

Figure 24:
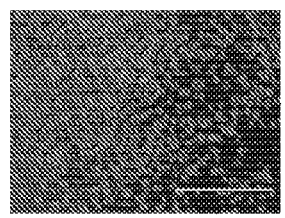
FIG. 24 is a microscopic photograph of a cell colony according to Example 2.
Figure 25:
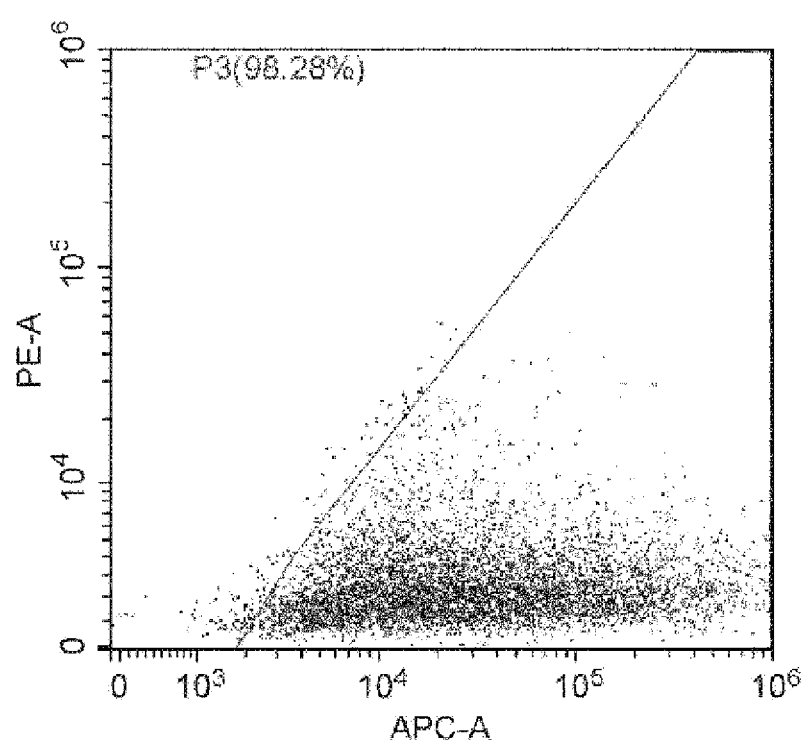
FIG. 25 is a histogram showing the results of flow cytometry of iPS cells according to Example 2.

When the iPS cells cultured in the culture vessel 30 were observed under a microscope, formation of uniform cell colonies was confirmed in all cases as shown in FIG. 24. Moreover, when the expressed amount of the cell surface antigen TRA-1-60 in the iPS cells was measured with a flow cytometer in the same manner as Example 1, roughly 100% of the iPS cells were TRA-1-60 positive on the 15th day after the start of culture as shown in FIG. 25.

Figure 23:
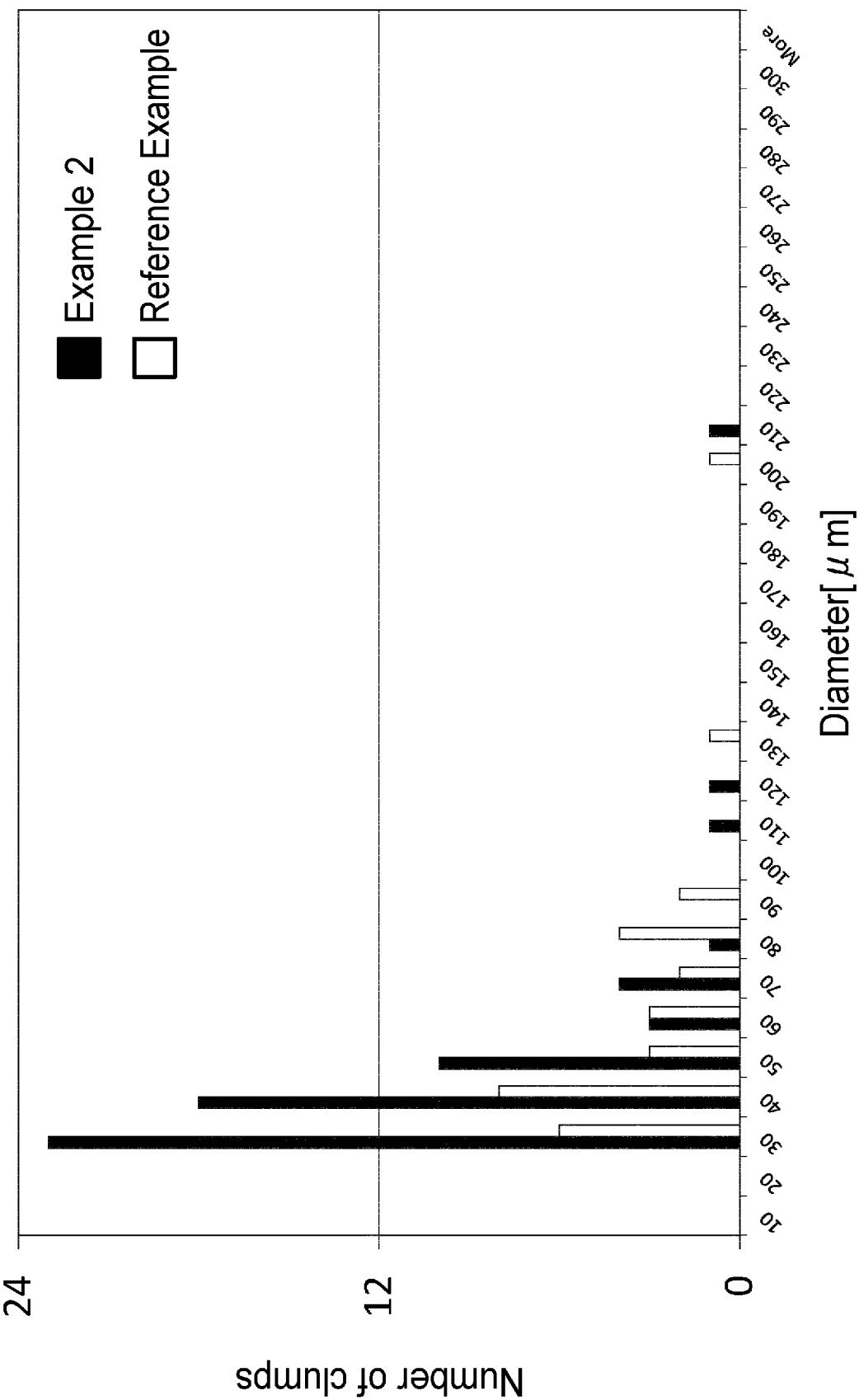
FIG. 23 is a histogram of the size of cell colonies according to a reference example and Example 2.

The sizes and numbers of the colonies of iPS cells cultured in a cell culture equipment similar to the cell culture equipment shown in FIG. 2 were measured, with the results shown in FIG. 23. More clumps were observed in comparison with the reference example. This shows that using a cell culture equipment improves cell viability and promotes the growth rate.

Example 3

A growth factor was added to medium (StemSpan H3000, registered trademark, Stemcell Technologies Inc.), and deacylated gellan gum was also added to the medium to prepare a gel medium.

The prepared gel medium was placed in a 15 mL tube and seeded with $2 \times 10^5$ blood cells. The 15 mL tube was then set in a $CO_2$ incubator, and the blood cells (mononuclear cells) were cultured for 7 days. A Sendai virus vector (CytoTune-iPS 2.0, ID Pharma Co., Ltd.) carrying OCT3/4, SOX2, KLF4 and cMYC was added to the medium to a multiplicity of infection (MOI) of 10.0 to infect the blood cells with the Sendai virus.

After addition of the Sendai virus to the gel medium, 15 mL of gelled stem cell medium (DMEM/F12 containing 20% KnockOut SR (registered trademark, Thermo Fisher Scientific)) was added to the gel medium, 15 mL of this medium containing cells infected with the Sendai virus was placed in the culture vessel 30 shown in FIGS. 17 and 18, and gel medium was also injected into the medium holding vessel 40. In the same manner as Example 1, the insides of the culture vessel 30 and the medium holding vessel 40 were sealed so that there was no gas exchange whatsoever between the insides and outsides of the culture vessel 30 and the medium holding vessel 40.

Suspension culture of the cells introduced with the initiation factor was initiated inside the culture vessel 30. Subsequently, 2 mL of new gel medium was substituted for 2 mL of the gel medium inside the medium holding vessel 40 once every 2 days.

Figure 26:
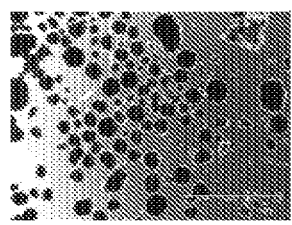
FIG. 26 is a microscopic photograph of a cell colony according to Example 3.
Figure 27:
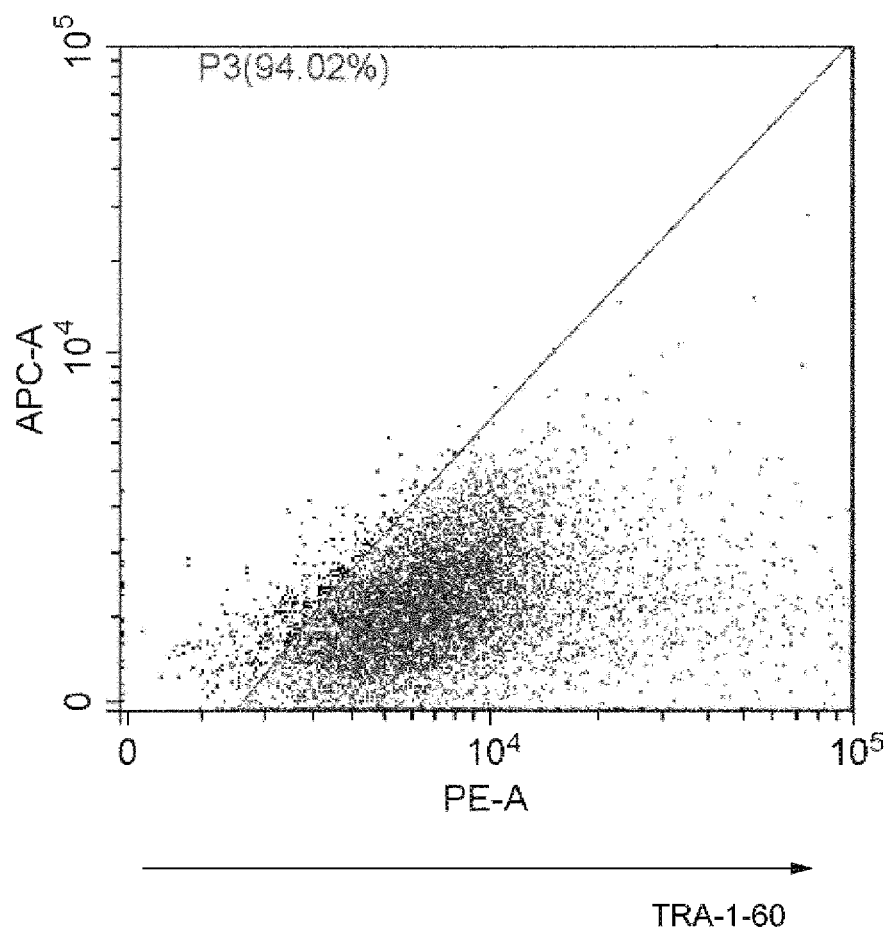
FIG. 27 is a histogram showing the results of flow cytometry of iPS cells according to Example 3.

When the cells were observed under a microscope after 15 days, formation of ES cell colonies was confirmed as shown in FIG. 26. When the cells were fixed with 4% paraformaldehyde and the expressed amount of the cell surface antigen TRA-1-60 in the fixed cells was measured with a flow cytometer, at least 90% of the cells were TRA-1-60 positive as shown in FIG. 27, confirming almost complete reprogramming. This shows that iPS cells can be induced from somatic cells other than stem cells without medium exchange or gas exchange in a completely sealed environment.

REFERENCE SIGNS LIST

10 Culture component permeable member
21 Culture-side plate
22 Medium-side plate
30 Culture vessel
31 Housing
32 Cover
33 Plug
34 Plug
40 Medium holding vessel
41 Rectifying plate
51 Introduction fluid machine
52 Discharge fluid machine
60 Medium tank
61 Plug
62 Plug
70 Conduit case
80 Driver holding member
82 Hole
90 Packing
110 Semipermeable membrane
131 Opening
132 Window 140 Opening
145 Discharge block
151 Pump head
152 Pump head
200 Medium conduit
231 Supply inlet
240 Inlet
241 Discharge port
242 Opening
251 Driver
252 Driver
331 Outlet
340 Outlet
351 Outside air shielding member for introduction fluid machine
352 Outside air shielding member for discharge fluid machine
401 Input device
402 Output device
403 Relationship storage
501 Image processer
511 Contour definer
512 Cell evaluator
513 Statistical processer
514 Density calculator
515 Medium evaluator

What is claimed is:

1. A cell culture equipment comprising:
a culture component permeable sheet that is permeable to culture components,
a culture vessel for holding a cell-containing medium and culturing cells that covers one side of the culture component permeable sheet,
a medium holding vessel for holding a medium that covers the other side of the culture component permeable sheet, and
a medium conduit connected to the medium holding vessel,
wherein the culture vessel comprises a culture vessel supply inlet for supplying a cell to the inside of the culture vessel and a culture vessel outlet for discharging a cell from the inside of the culture vessel,
wherein the medium conduit is sealable,
wherein the medium conduit comprises
a medium conduit supply inlet for supplying fluid to the inside of the medium conduit and a medium conduit outlet for discharging fluid from inside the medium conduit,
wherein
the medium conduit supply inlet and medium conduit outlet are sealable,
the cell culture equipment further comprises
a fluid machine for transporting the fluid in the medium conduit, and a shield on which the medium conduit and the fluid machine are disposed, and
wherein
the medium conduit and a pump head of the fluid machine are disposed inside of the shield, while a driver connected to the pump head of the fluid machine is disposed outside of the shield.

2. The cell culture equipment according to claim 1, wherein a supply equipment for supplying fluid to the medium conduit supply inlet is detachable.

3. The cell culture equipment according to claim 1, wherein a discharge equipment for discharging the fluid from the medium conduit outlet is detachable.

4. The cell culture equipment according to claim 1, wherein
a supply equipment for supplying fluid to the medium conduit supply inlet is detachable,
a discharge equipment for discharging the fluid to the medium conduit outlet is detachable, and
fluid inside the medium conduit moves to the inside of the discharge equipment in the case where fluid is supplied from the supply equipment to the inside of the medium conduit.

5. The cell culture equipment according to claim 4, wherein air inside the medium conduit moves to the inside of the discharge equipment in the case where medium is supplied to the inside of the medium conduit from the supply equipment.

6. The cell culture equipment according to claim 4, wherein the medium inside the medium conduit moves to the inside of the discharge equipment in the case where medium is supplied to the inside of the medium conduit from the supply equipment.

7. The cell culture equipment according to claim 4, wherein outside air does not enter the inside of the medium conduit in the case where fluid is supplied to the inside of the medium conduit from the supply equipment.

8. The cell culture equipment according to claim 1, wherein
a supply equipment for supplying fluid to the medium conduit supply inlet is detachable,
a discharge equipment for discharging the fluid to the medium conduit outlet is detachable, and
the fluid is supplied from the supply equipment to the medium conduit and the fluid inside the medium conduit moves to the inside of the discharge equipment in the case where the fluid machine is operated.

9. The cell culture equipment according to claim 1, wherein outside air does not enter the medium conduit in the case where the medium conduit is in a sealed state.

10. The cell culture equipment according to claim 1, wherein microorganisms, viruses and dust from outside the medium conduit do not enter the medium conduit in the case where the medium conduit is in a sealed state.

11. The cell culture equipment according to claim 1, wherein substances inside the medium conduit do not leak out of the medium conduit in the case where the medium conduit is in a sealed state.

12. The cell culture equipment according to claim 1, wherein there is no exchange of gasses between the inside and outside the medium conduit in the case where the medium conduit is in a sealed state.

13. The cell culture equipment according to claim 1, wherein the medium inside the medium conduit is maintained within a predetermined pH range.

14. The cell culture equipment according to claim 1, wherein the medium conduit is embedded in a gas impermeable material.

15. The cell culture equipment according to claim 1, wherein at least part of the medium conduit is a hole provided in a gas impermeable material.

16. The cell culture equipment according to claim 1, wherein the fluid machine is shielded from outside air by an outside air shield for the fluid machine.

17. The cell culture equipment according to claim 1, wherein the pump head and the driver are detachable.

18. The cell culture equipment according to claim 17, wherein
the driver is supported on a driver holder, and
the medium conduit and the driver holder are detachable.

19. The cell culture equipment according to claim 1, wherein cells are cultured inside the medium conduit.

20. The cell culture equipment according to claim 1, further comprising:
   an image apparatus for imaging at least either one of the medium and the cells inside the medium conduit.

* * * * *